(12) United States Patent
Marx et al.

(10) Patent No.: US 7,504,374 B2
(45) Date of Patent: Mar. 17, 2009

(54) METHOD FOR INDUCING DEPOSITION AND MATURATION OF BONE COMPRISING A CO-THERAPEUTIC REGIMEN OF LMP-1 AND BMP-2

(75) Inventors: Jeffrey C. Marx, Germantown, TN (US); William F. McKay, Memphis, TN (US); Scott D. Boden, Atlanta, GA (US)

(73) Assignees: Warsaw Orthopedic, Inc.; Emory University

( * ) Notice: Subject to any disclaimer, the term of this patent is extended or adjusted under 35 U.S.C. 154(b) by 3 days.

(21) Appl. No.: 11/385,612

(22) Filed: Mar. 21, 2006

(65) Prior Publication Data

US 2007/0027081 A1 Feb. 1, 2007

Related U.S. Application Data

(63) Continuation-in-part of application No. 10/399,830, filed as application No. PCT/US01/46044 on Oct. 24, 2001.

(60) Provisional application No. 60/772,322, filed on Feb. 10, 2006, provisional application No. 60/736,191, filed on Nov. 10, 2005, provisional application No. 60/664,074, filed on Mar. 22, 2005, provisional application No. 60/664,073, filed on Mar. 22, 2005, provisional application No. 60/242,794, filed on Oct. 24, 2000.

(51) Int. Cl.
  *A61K 38/16* (2006.01)
  *A61K 38/17* (2006.01)
  *A61K 38/18* (2006.01)
  *A61K 38/19* (2006.01)

(52) U.S. Cl. ............... 514/2; 514/7; 514/8; 514/12

(58) Field of Classification Search ............. None
See application file for complete search history.

(56) References Cited

U.S. PATENT DOCUMENTS

| | | | |
|---|---|---|---|
| 6,300,127 B1 | 10/2001 | Hair et al. | |
| 2003/0138473 A1* | 7/2003 | Koblish et al. | 424/423 |
| 2004/0034428 A1* | 2/2004 | McKay | 623/17.16 |
| 2006/0019392 A1 | 1/2006 | Hair et al. | |

FOREIGN PATENT DOCUMENTS

WO   WO 2004/043333   *   5/2004

OTHER PUBLICATIONS

Groeneveld et al., 2000, Eur. J. Endocrinol. 142 :9-21.*
Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Neely et al., Transcription activator interactions with multiple SWI/SNF subunits; Molecular and Cellular Biology, 2002; vol. 22, No. 6, pp. 1615-1625.
Liu et al., Overexpressed LIM mineralization proteins do not require LIM domains to induce bone; Journal of Bone and Mineral Research, 2002; vol. 17, pp. 406-414.
Murakami et al, Cooperative inhibition of bone morphogenetic protein signaling by smurf1 and inhibitory smads; Molecular Biology of the Cell, 2003; vol. 14, pp. 2809-2817.
Itoh et al., Promoting bone morphogenetic protein signaling through negative regulation of inhibitory smads; The EMBO Journal, 2001; vol. 20, No. 15, pp. 4132-4142.
Suzuki et al, Smurf1 regulates the inhibitory activity of smad7 by targeting smad7 to the plasma membrane; The Journal of Biological Chemistry, 2002; vol, 277, No. 42, pp. 39919-39925.
Brannetti et al, iSPOT: a web tool to infer the interaction specificty of families of protein modules; Nucleic Acids Research, 2003; vol. 31, No. 13, pp. 3709-3711.
Holen, Torgeir, Mechanisms of RNAi: mRNA cleavage fragments may indicate stalled RISC; Journal of RNAi and Gene Silencing, 2005; vol. 1, No. 1, pp. 21-25.
Kim et al., Jab1/CSN5, a component of the COP9 signalosome, regulates transforming growth factor-β signaling by binding to smad7 and promoting its degradation, 2004; Molecular and Cellular Biology; vol. 24, No. 6, pp. 2251-2262.
Lee et al., Sumoylation of smad4, the common smad mediator of transforming growth factor-β family signaling; The Journal of Biological Chemistry, 2003; vol. 278, No. 30, pp. 27853-27863.
Moren et al., Differential ubiquitination defines the functional status of the tumor suppressor smad4; The Journal of Biological Chemistry, 2003; vol. 278, No. 35, pp. 33571-33582.
Boden et al., LMP-1, a LIM-domain protein, mediates BMP-6 effects on bone formation; Endocrinology, 1998; vol. 139, No. 12, pp. 5125-5134.
Murillas et al., Identification of developmentally expressed proteins that functionally interact with Nedd4 ubiquitin ligase; The Journal of Biological Chemistry, 2002; vol. 277, No. 4, pp. 2897-2907.
Wan et al., Jab1 antagonized TGF-β signaling by inducing smad4 degradation; EMBO reports, 2002; vol. 3,No. 2, pp. 171-176.
Maeda et al., Endogenous TGF-β signaling suppresses maturation of osteoblastic mesenchymal cells; The EMBO Journal, 2004; vol. 23, No. 3, pp. 552-563.
Ebisawa et al., Smurf1 interacts with transforming growth factor-β type I receptor through smad7 and induces receptor degradation; The Journal of Biological Chemistry, 2001; vol. 276, No. 16, pp. 12477-12480.
Murakami et al., Cooperative Inhibition of Bone Morphogenetic Protein signaling by smurf1 and inhibitory smads; Molecular Biology Of The Cell, 2003; vol. 14, pp. 2809-2817.

* cited by examiner

*Primary Examiner*—Elizabeth C. Kemmerer
(74) *Attorney, Agent, or Firm*—Fox Rothchild LLP

(57) ABSTRACT

The present invention relates to the methods and compositions for the treatment of subjects having compromised bone conditions. Specifically, the invention relates to combinatorial therapeutic strategies including small molecules and peptide mimics of LIM mineralization proteins, particularly LMP-1, to overcome the dose-related translational barriers for BMP-2 therapeutics.

19 Claims, No Drawings

METHOD FOR INDUCING DEPOSITION AND MATURATION OF BONE COMPRISING A CO-THERAPEUTIC REGIMEN OF LMP-1 AND BMP-2

RELATED APPLICATION(S)

This application claims the benefit of U.S. Provisional Application No. 60/664,073, filed on Mar. 22, 2005, U.S. Provisional Application No. 60/664,074, filed on Mar. 22, 2005, U.S. Provisional Application No. 60/736,191, filed on Nov. 10, 2005 and U.S. Provisional Application No. 60/772,322, filed on Feb. 10, 2006. The entire teachings of the above applications are incorporated herein by reference. This application is also a continuation-in-part application of U.S. application Ser. No. 10/399,830 which entered U.S. national stage on Jul. 25, 2003 from PCT application PCT/US01/46044 filed on Oct. 24, 2001, which claims benefit of U.S. Provisional Application Ser. No. 60/242,794, filed on, Oct. 24, 2000.

BACKGROUND OF THE INVENTION

Many Americans are afflicted by low back pain, degenerative spinal disease, or bone fractures. These musculoskeletal problems are responsible for a major portion of the health care budget and are among the greatest causes of chronic disability and lost productivity in the United States. Orthopaedic surgical treatment of these problems frequently requires bone grafting to promote healing. Fusion of two or more bones with cancellous bone graft may fail to heal in 25-45% of patients, and in even higher percentage of smokers and diabetic patients, co-morbidities which are more prevalent in the Veteran population. Use of osteoinductive proteins such as BMP-2 to induce bone formation in these patients is now possible. In 2002 the U.S. Food and Drug Administration approved rhBMP-2 for use as a bone graft substitute in interbody spine fusions. Despite this regulatory milestone for BMP-2, this technology is not feasible for many patients with bone healing needs due to an unexpectedly high dose required in humans which has resulted in a very high cost (Boden S D, Zdeblick T A, Sandhu H S, and Heim S E. *Spine* 2000;25: 376-81; Ackerman S J, Mafilios M S, and Polly D W, Jr. *Spine* 2002;27:S94-S99).

A 15,000-fold higher concentration of BMP-2 is required to induce bone in humans (1.5 mg/mL) than in cell culture (100 ng/mL). Thus, without a dramatic improvement in BMP-2 responsiveness, healthcare economics may severely limit translation of one of the most seminal discoveries related to osteoblast differentiation in the last 50 years from helping large numbers of patients.

Consequently, a further understanding of the complex regulation of BMP-2 during osteoblast differentiation and the cellular responsiveness to such important bone forming proteins is critical so that their effect can be enhanced or their required dose limited to a more affordable quantity of protein especially in the most challenging orthopaedic healing environment—posterolateral lumbar spine fusion.

Several years ago a novel intracellular LIM domain protein critical to fetal and post-natal bone formation was identified (Boden S D, Liu Y, Hair G A et al. *Endocrinology* 1998;139: 5125-34).

Termed LIM Mineralization Protein (LMP-1) it was the first LIM domain protein to be directly associated with osteoblast differentiation. Blocking LMP-1 expression prevents osteoblast differentiation in vitro, suggesting a critical functional role of this novel intracellular protein. Leukocytes expressing the LMP-1 cDNA (via plasmid or adenoviral transduction) that are implanted into rabbits or athymic rats induce bone formation in bony and ectopic locations (Boden S D, Titus L, Hair G et al. *Spine* 1998;23:2486-92). The feasibility of LMP-1 delivery by ex vivo gene therapy for spine fusion and bone defect applications in rabbits and primates is currently being evaluated. LMP-1 also has considerable potential as a local, regional, or systemic anabolic strategy for increasing bone density in patients with osteoporosis. However, before clinical applications can be seriously considered it will be critical to understand the mode of action of this protein. The present invention addresses this problem.

Osteoblasts are thought to differentiate from pluripotent mesenchymal stem cells, the maturation of which results in the secretion of an extracellular matrix which can mineralize and form bone. The regulation of this complex process involves a group of signaling glycoproteins known as bone morphogenetic proteins (BMPs), members of the transforming growth factor-beta (TGF-β) superfamily. Some BMPs are uniquely capable of initiating the entire osteoblast differentiation cascade and BMP-2 is one of the most extensively studied.

With Applicant's discovery that LMP-1 can dramatically increase cellular responsiveness of mesenchymal stem cells (MSCs) to BMP-2 and mechanistic elucidation of various aspects of the signaling pathway of LMP-1, the present invention provides combinatorial strategies including small molecules and peptide mimics, to overcome the dose-related translational barriers for BMP-2 therapeutics.

SUMMARY OF THE INVENTION

The present invention relates to combinatorial therapeutic strategies including small molecules and peptide mimics of LIM mineralization proteins, primarily LMP-1, to overcome the dose-related translational barriers for BMP-2 therapeutics.

DETAILED DESCRIPTION

The present invention derives from studies designed to elucidate the mechanism of LIM mineralization protein (LMP) action in modulating growth factor responsiveness in cells, tissues and organisms. As a result of these studies, Applicant's have discovered that there is an unexpected synergistic result when an osteogenic composition comprising at least one LIM mineralization protein and at least one growth factor is administered to induce bone formation in a subject in need of bone repair, replacement or augmentation, for example subject suffering from compromised bone conditions.

Overview

The studies disclosed herein demonstrate that LMP-1 enhances responsiveness to BMP-2 in MSCs. To elucidate the mechanism underlying this observation it is further demonstrated that LMP-1 interacts in vitro with an 85 kDa protein, identified as Smurf1, a key regulator of the degradation of BMP-2 signaling molecules, Smad1 and Smad5. It is also demonstrated here that endogenous Smurf1 and LMP-1 co-immunoprecipitate from cells, suggesting the physiological relevance of the interaction. The importance of the Smurf1/LMP-1 interaction is further documented by the fact that LMP-1 overexpression increases levels of phosphorylated Smad1 (P-Smad1) in the nucleus and increases expression of BMP-2 regulated genes, expected outcomes of Smurf1/

LMP-1 interaction. LMP-1-induced inhibition of Smurf1 WW domain antibody binding to Smurf identified the WW domain as the region of Smurf1 that LMP-1 binds. Further, analysis of LMP-1 sequence has identified two potential WW domain interacting motifs within an osteoinductive region of LMP-1. It is also demonstrated that LMP-1 increases BMPR1A levels in support of the hypothesis that LMP interrupts the Smurf1/Smad6 mediated degradation of the BMP receptor. LMP-1 is shown herein to interact with Jab1, an adaptor protein which regulates degradation of the common Smad, Smad4 resulting in increased nuclear Smad4.

Furthermore, identified herein is the precise region of LMP which interacts with Smurf1. This discovery facilitates design of small compounds that mimic LMP's effects. The compounds include small proteins and peptides. In addition, the ability to use a single exposure dose of a recombinant TAT-LMP fusion protein is demonstrated, confirming that continuous LMP-1 expression is not required for an effective therapeutic outcome and opens the door for design of an LMP-mimic small compound.

Also discovered is a novel interaction between LMP-1 and Smurf1 which represents a powerful control mechanism over BMP signaling and responsiveness. This LMP-1 interaction occurs with the Smurf WW2 domain, is dependent on a specific PY motif in LMP-1, and can be mimicked by a small peptide containing only that motif. Further, LMP-1 competitively binds to Smurf1, preventing ubiquitin-mediated proteasomal degradation of Smads, contributing to an enhanced cellular responsiveness to BMP-2. These findings allow for the design of small molecule therapeutics that more efficiently control responsiveness of the BMP signaling pathway which would make clinical translation easier. Such small molecules would be more easily synthesized, stored, and delivered for clinical use to induce bone formation alone or with much lower doses of BMP-2 than are currently required in the clinical setting.

Thus, therapeutics that modulate the effects of LMP-1 have the potential to either replace BMP-2 as a strategy to induce bone formation or to serve as a method to enhance the efficacy of rhBMP-2, lowering the dose and cost of its use as an inducer of bone formation.

Combination Therapy

The invention relates to treatment of diseases using combination therapy. In particular, the novel LMP agents described herein may be used in conjunction with BMP agents. The present invention provides a method of inducing bone deposition by co-administration of at least one LMP agent and a therapeutically effective dose of at least one BMP agent. It has been found that LMP agents are capable of accelerating bone formation by enhancing the BMP agent's responsiveness. In the method of the invention, the LMP agent accomplishes this by affecting a BMP agent including but not limited to endogenous BMP protein, exogenous BMP protein, exogenous BMP protein fragment, and exogenous BMP protein variant fragment. The present invention may therefore be used to decrease the time required to form new bone in the presence of a BMP agent comprising administering at least one LMP agent.

As used herein LIM mineralization protein (LMP) "LMP" includes LMP-1 and biologically active fragments thereof, LMP1t and biologically active fragments thereof, and LMP-3 and biologically active fragments thereof. More detailed descriptions, including sequences, can be found in U.S. Pat. No. 6,300,127, pending application U.S. Ser. No. 10/951,236, and pending application U.S. Ser. No. 09/959,578 filed by Boden et al., the entire teachings of which are incorporated herein by reference. LMP-2 is excluded as it is non-osteogenic. Growth factors suitable in the invention include bone morphogenic proteins (BMP) including BMP-2.

As used herein the term "LMP agent" includes a functional fragment of an LMP protein, a functional fragment of an LMP protein with a protein transduction domailn (PTD) attached, an LMP protein with a PTD attached, an LMP protein without a PTD attached, a functional fragment of an LMP protein variant, an LMP protein variant with a PTD attached, an LMP protein variant without a PTD attached, an oligonucleotide sequence encoding any of the above, and an LMP gene.

As used herein, the term "BMP agent" includes a functional fragment of a BMP protein, a functional fragment of a BMP protein with a PTD attached, a BMP protein, a functional fragment of a BMP protein variant, a BMP protein variant, an endogenous BMP protein, exogenous BMP protein, an exogenous BMP protein fragment, an exogenous BMP protein variant fragment, an oligonucleotide sequence encoding any of the above, and a BMP gene. Particularly useful BMP is BMP-2, especially rhBMP-2.

Protein and Peptide Variants and Derivatives

Those skilled in the art will understand that one may make many molecules derived in sequence from the aforementioned LMP agents or BMP agents in which amino acids have been deleted ("deletion variants"), inserted ("addition variants"), or substituted ("substitution variants"). Molecules having such substitutions, additions, deletions, or any combination thereof are termed individually or collectively "variant(s)." Such variants should, however, maintain at some level (including a reduced level) the relevant activity of the unmodified or "parent" molecule (e.g., an LMP variant possesses the ability to modulate BMP responsiveness or to bind Smurf1). Hereinafter, "parent molecule" refers to an unmodified molecule or a variant molecule lacking the particular variation under discussion. There are two principal variables in the construction of amino acid sequence variant(s): the location of the mutation site and the nature of the mutation. In designing variant(s), the location of each mutation site and the nature of each mutation will depend on the biochemical characteristic(s) to be modified. Each mutation site can be modified individually or in series, e.g., by (1) deleting the target amino acid residue, (2) inserting one or more amino acid residues adjacent to the located site or (3) substituting first with conservative amino acid choices and, depending upon the results achieved, then with more radical selections.

An amino acid sequence addition may include insertions of an amino- and/or carboxyl-terminal fusion ranging in length from one residue to one hundred or more residues, as well as internal intra-sequence insertions of single or multiple amino acid residues. Internal additions may range generally from about 1 to 20 amino acid residues, preferably from about 1 to 10 amino acid residues, more preferably from about 1 to 5 amino acid residues, and most preferably from about 1 to 3 amino acid residues. An example of an amino- or a carboxy-terminus addition includes chimeric proteins comprising the amino-terminal or carboxy-terminal fusion of the parent molecules with all or part of a transduction peptide or other conjugate moiety.

Amino acid sequence deletions generally range from about 1 to 30 amino acid residues, preferably from about 1 to 20 amino acid residues, more preferably from about 1 to 10 amino acid residues and most preferably from about 1 to 5 contiguous residues. Amino-terminal, carboxy-terminal and internal intrasequence deletions are contemplated by the present invention. As used herein a "functional fragment" of a protein is any fragment or portion of a protein which retains the characteristic of interest of the parent protein or peptide. As used herein "biologically active" means retaining that characteristic or property in question from the parent molecule.

In one embodiment the protein or peptide may possess multiple activities such as would be provided by multiple binding sites. These binding sites or domains may be identical or variable and may be in sequence or separated by non-binding site amino acids.

In yet another embodiment, recombinant proteins, peptides or fusion proteins may be produced.

In another embodiment the LMP agents or BMP agents of the present invention are conjugated to other proteins or peptides. Protein transduction domains (PTDs) and attachment of these to proteins and peptides are contemplated. In one embodiment of the present invention, the PTD is the HIV-TAT protein.

In one embodiment, a variant protein or peptide will preferably be substantially homologous to the amino acid of the parent molecule or a portion or a domain of the parent molecule from which it is derived. The term "substantially homologous" as used herein means a degree of homology that is in excess of 80%, preferably in excess of 90%, more preferably in excess of 95% or most preferably even 99%. Homology is determined relative to the smaller peptide or variant and is measured across that domain, site or fragment in the parent from which the variant or peptide is derived.

The invention also comprises chemically modified derivatives of the parent molecule(s) in which the peptide is linked to a nonproteinaceous moiety (e.g., a polymer) in order to modify its properties. These chemically modified molecules are referred to herein as "derivatives". Such derivatives may be prepared by one skilled in the art given the disclosures herein. Conjugates may be prepared using glycosylated, non-glycosylated or de-glycosylated parent molecule(s) and suitable chemical moieties. Typically non-glycosylated molecules and water-soluble polymers will be used. Other derivatives encompassed by the invention include post-translational modifications (e.g., N-linked or O-linked carbohydrate chains, processing of N-terminal or C-terminal ends), attachment of chemical moieties to the amino acid backbone, and chemical modifications of N-linked or O-linked carbohydrate chains. The polypeptides may also be modified with a detectable label, such as an enzymatic, fluorescent, isotopic or affinity label to allow for detection and isolation of the protein peptide.

Water-soluble polymers are desirable because the protein or peptide to which each is attached will not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically and, if so, the therapeutic profile of the protein (e.g., duration of sustained release; resistance to proteolysis; effects, if any, on dosage; biological activity; ease of handling; degree or lack of antigenicity and other known effects of a water-soluble polymer on a therapeutic proteins).

Variants and/or derivatives may be screened to assess their physical properties in vitro and can be subsequently screened in vivo in the models described herein. It will be appreciated that such variant(s) will demonstrate similar properties to the unmodified molecule but not necessarily all of the same properties and not necessarily to the same degree as the corresponding parent molecule.

Oligonucleotides

Oligonucleotide sequences of the present invention include those polymeric nucleic acid sequences which would "code for" the protein or peptide of interest. Those of ordinary skill in the art will appreciate the degeneracy of the genetic code and that variable codons may still produce the same protein on translation. As used herein the term "oligonucleotide" includes nucleic acid sequences which code for the proteins or peptides of the invention or their parent molecules, including but not limited to the LMP and BMP agents and vectors encoding said agents as well as small interfering RNAs (siRNAs) designed to target the genes disclosed herein, especially those involved in BMP and LMP signalling pathways. Particular oligonucleotides of the present invention include siRNAs designed to LMP-1, Smurf1, Smurf2 and Jab1.

Pharmaceutical Compositions

The invention also provides for pharmaceutical compositions in the form of an osteogenic composition. As used herein an "osteogenic composition" is a composition comprising a therapeutically effective amount of at least one BMP agent combined with at least one other agent and optionally, at least one pharmaceutically acceptable diluent, carrier, solubilizer, emulsifier, preservative and/or adjuvant. In a preferred embodiment, the osteogenic composition comprises a therapeutically effective amount of at least one LMP agent and at least one BMP agent and optionally, at least one pharmaceutically acceptable diluent, carrier, solubilizer, emulsifier, preservative and/or adjuvant. It is understood that the phrase "at least one" includes one and more than one; for example, two, three, four or more.

In another embodiment an osteogenic composition comprises at least one Smurf binding agent; and at least one BMP agent; and optionally, at least one pharmaceutically acceptable diluent, carrier, solubilizer, emulsifier, preservative and/or adjuvant. In the present invention, Smurf binding agents include LMP-1 protein, and LMP-1 protein fragments, variants or derivatives, and siRNA specific for Smurf mRNA. The Smurf is selected from the group consisting of Smad Ubiquitin Regulatory Factor-1 (Smurf1) and Smurf 2.

In yet another embodiment, the osteogenic composition comprises at least one phosphorylated Smad 1 competitive binding agent and at least one BMP agent. In the present invention, the phosphorylated Smad 1 competitive binding agent includes but is not limited to an LMP-1 protein, and LMP-1 protein fragment, variant or derivative, and siRNA specific for phosphorylated Smad 1.

In another embodiment, the osteogenic composition comprises at least one phosphorylated Smad 5 competitive binding agent and at least one BMP agent. In the present invention, the phosphorylated Smad 5 competitive binding agent includes but is not limited to an LMP-1 protein, and LMP-1 protein fragment, variant or derivative, and siRNA specific for phosphorylated Smad 5.

Also disclosed is an osteogenic composition comprising at least one phosphorylated Smad 4 competitive binding agent and at least one BMP agent. In the present invention, the phosphorylated Smad 4 competitive binding agent includes but is not limited to an LMP-1 protein, and LMP-1 protein fragment, variant or derivative, siRNA specific for phosphorylated Smad 4.

Pharmaceutically acceptable diluents, carriers, solubilizers, emulsifiers, preservatives and/or adjuvants are known to those skilled in the art. These include but are not limited to cells, vectors, gels, microspheres, macromolecules, biocompatible foams, biocompatible matrices, and implants. Compositions may also comprise incorporation of any of the therapeutic molecules or agents into liposomes, microemulsions, micelles or vesicles for controlled delivery over an extended period of time. The term "therapeutically effective amount" means an amount which provides a therapeutic effect for a specified condition and route of administration. Whether an amount is therapeutically effective may be determined on a stand alone or combinatorial basis. Consequently, what might represent a therapeutically effective amount of one agent may change when that agent is combined with a further agent. In a preferred embodiment of the invention, an LMP agent is administered in combination with a BMP agent, wherein the dose or amount of BMP agent is subtherapeutic as compared to conventional rhBMP-2 therapy alone. As a stand alone therapy, a BMP agent at subtherapeutic doses or amounts would not, therefore, be therapeutically effective but when combined with the LMP agents of the present invention would represent a therapeutic dose or amount.

Administration and Dose

Depending on dosage form, the pharmaceutical compositions of the present invention may be administered in different ways, i.e., intrathecal injection, subcutaneous, intravenous, intraperitoneal, intramuscular injection, in an implant or combinations thereof. The administration of the LMP agents of the present invention may occur before, after or simultaneously with the BMP agent and may be to a single targeted site or separate sites. Sites for administration include, but are not limited to an intervertebral space, a facet joint, site of a bone fracture, bones of the mouth, chin and jaw, and an implant site.

In yet another embodiment, the therapeutic methods of the invention further comprises a co-therapeutic treatment regimen comprising administering a therapeutically effective amount of an LMP agent in combination with a therapeutically effective amount of a BMP agent to treat disease in a patient. As used herein a "co-therapeutic treatment regimen" means a treatment regimen wherein two agents are administered simultaneously, in either separate or combined formulations, or sequentially at different times separated by minutes, hours or days, but in some way act together to provide the desired therapeutic response.

Dosages of the LMP agent, BMP agent or compositions of the present invention may range from 1 nM to 200 nM if delivered as a recombinant fusion protein with a PTD attached or from 0.1 to 100 MOI (multiplicity of infection, i.e. number of infectious viral particles per cell) if delivered by an adenovirus or similar vector. In combination, it is understood that doses of one agent may be lowered when the dose of a co-administered agent is raised. For example, it is contemplated that on raising the dose of an LMP agent, the dose of the BMP agent administered may be lowered. It is also contemplated with synergistic compositions, that administration of one component of a combination will mitigate the need for an equal dose of a second component as is demonstrated herein with the LMP agent synergistically increasing the responsiveness of cells to a BMP agent.

In one embodiment, therapeutically effective dose of BMP agent is less than the currently acceptable therapeutically effective amount. Currently, 1.5 mg/mL of bone formed is the therapeutic concentration of rhBMP-2 in primates in vivo with smaller doses effective in cell culture and rodents. The therapeutically effective dose of said at least one BMP agent is at least 10-fold less than the dose required in conventional therapy. The dose required in conventional therapy can be 20 mg rhBMP-2 per site of 10 cc of bone formation. In other embodiments, the therapeutically effective dose of BMP is at least 20-fold, 50-fold, 100-fold, 1000-fold, 5000-fold or 10,000-fold less than the dose required in conventional BMP therapy when administered in combination with an LMP agent.

Treatment Outcomes

The therapeutic agents and compositions of the present invention are useful in treating subjects having compromised bone conditions. The invention provides for a method of treating a bone disorder using a therapeutically effective amount of an LMP agent in combination with a BMP agent. The bone disorder or compromised bone condition may be any disorder characterized by bone loss (osteopenia or osteolysis) or by bone damage or injury. Such bone conditions include but are not limited to broken bones, bone defects, bone transplant, bone grafts, bone cancer, joint replacements, joint repair, fusion, facet repair, bone degeneration, dental implants and repair, bone marrow deficits and other conditions associated with bone and boney tissue.

Examples of bone defects include but are not limited to a gap, deformation or a non-union fracture in a bone.

Examples of bone degeneration include but are not limited to osteopenia or osteoporosis. In one embodiment, the bone defect is due to dwarfism.

The invention is especially useful for joint replacement or repair wherein the joint is vertebral, knee, hip, tarsal, phalangeal, elbow, ankle, sacroiliac or other articulating/non-articulating joint.

Bone Tissue Engineering

Furthermore, the engineering and use of cell- and animal-based models of bone disease in which the compounds of the invention may be useful are also described. The invention includes a process for engineering bone tissue comprising combining at least one LMP agent and at least one BMP agent with a cell selected from the group consisting of osteogenic cells, pluripotent stem cells, mesenchymal cells, and embryonic stem cells. Also, disclosed is the engineered bone tissue produced by the above process. A method for inducing bone formation in a subject comprising administering the engineered bone tissue of the present invention is contemplated.

Further, the invention includes a process for engineering bone tissue comprising combining at least one phosphorylated Smad 4 competitive binding agent and at least one BMP agent with a cell selected from the group consisting of osteogenic cells, pluripotent stem cells, mesenchymal cells, and embryonic stem cells. Also included is engineered bone tissue produced by this process. In another aspect, the invention includes a method for inducing bone formation in a subject comprising administering the engineered bone tissue as described in this paragraph.

Also included in the invention is a method for inducing deposition and maturation of bone in a subject having compromised bone conditions comprising administering to the subject at least one Jab1-inhibiting agent and a therapeutically effective dose of at least one BMP agent.

Methods and Procedures

Cell culture: Mesenchymal stem cells, (MSCs) at passage 2 are purchased from Cambrex Bio Sciences. Cells are grown at 37° C. in 5% $CO_2$ in MSCBM media supplemented with MSCGM Singlequots (Cambrex Bio Sciences), split at confluence, and plated at $3\times10^4$ cells/well in 6-well dishes at passage 4 in these studies. The next day treatments are applied in the presence of 50 uM L-Ascorbic Acid 2-Phosphate and 5 mM β-glycerol phosphate (Sigma-Aldrich). Medium is changed every 3-4 days with re-application of treatments where appropriate. Cells are transduced for 30 min with adenoviral constructs in 0.5 ml serum free medium. rhBMP-2 will continue to be supplied as a gift from Wyeth (Genetics Institute) courtesy of John Wozney.

Preparation of nuclear and cytoplasmic protein fractions: Cell pellets are suspended in buffer A (20 mM HEPES, pH 7.9, 10 mM KCl, 1 mM EGTA, 1 mM EDTA, 0.2% Nonidet P-40, 10% Glycerol, 1 mM PMSF and 1 ug/ml protease inhibitor mix (Sigma)), incubated on ice for 10 min, and centrifuged. Supernatants (cytoplasmic fraction) are collected and nuclear pellets are suspended in high salt buffer B (buffer A plus 600 mM KCl, 20% glycerol), incubated on ice for 30 min and centrifuged. Supernatants are collected as the nuclear fraction. After protein determination, fractions are subjected to SDS-PAGE.

Measurement of phosphorylated Smad1 and Smad5 in the nucleus on overexpression of LMP-1: To show that increased levels of LMP-1 result in increased levels of phosphorylated Smad1 and Smad5, hMSCs are treated with the doses of LMP-1 that successfully synergize with BMP-2 to determine the timecourse of increased of phosphorylated Smad1 in the nucleus when the agents are applied alone or together.

Human MSCs are plated at $3 \times 10^4$ cells/well in 6-well plates, grown overnight, and treated with Ad5F35-LMP-1 (0, 5, 10 pfu/cell), BMP-2 (100 ng/ml) or both agents (control=Ad5F35-GFP). After 1, 2, 4, 8, 12, 24 and 48 hrs, cells are harvested and nuclear proteins are analyzed by Western blot for Smad proteins. Both Smad1 and Smad5 are measured. Antibody to phosphorylated Smad1 is available and is used for Western analysis. Antibody to phosphorylated Smad5 is not available so an antibody that detects both phosphorylated and unphosphorylated Smad5 is used; and a phosphoserine antibody on a separate blot is used to determine the phosphorylation state. Although there will be several molecules having phosphoserine, comparison of the two blots should allow determination of whether P-Smad5 also increases in the nucleus. Treating cells with the same adenoviral vector carrying GFP cDNA as a control is not expected to have an effect on nuclear levels of P-Smads. Increased P-Smad levels are expected to occur rapidly in response to BMP-2, since that involves phosphorylation of existing Smad proteins to activate the intracellular signaling cascade. In contrast, LMP-1 cDNA must be transcribed and translated into an intracellular protein, a process requiring several hours. Thus a delay in increased nuclear levels of P-Smads is expected in response to LMP-1 as compared to the response to BMP-2.

SDS-PAGE and Westen blotting: SDS-PAGE is performed using 10% gels and transferred to nitrocellulose membrane. The membrane is blocked with milk protein, incubated with specific antibody, washed with Tris Buffered Saline containing 0.1% Tween 20 (TBST), incubated with anti-rabbit goat IgG-linked to horseradish peroxidase (NEN), and again washed with TBST. Chemiluminescent substrates are applied to the membrane and the signal is detected by exposing the membrane to X-ray film 30 seconds.

RNA extraction: RNA is isolated from cells grown in 6-well plates using RNeasy Mini Kits as specified by the manufacturer (Qiagen). Briefly, cells are harvested and disrupted in RLT buffer. The lysate is passed over QiaShredder columns, and the resulting eluate brought to 35% EtOH and passed over RNeasy columns to bind the RNA to the silica-gel membrane. After washing the bound RNA with RW1 buffer and then RPE buffer, the RNA is eluted from the membrane with water. All RNA samples are DNase treated either using the Qiagen RNase-Free DNase Set during the RNeasy procedure or after final harvest of the RNA using the Ambion DNA-free Kit. After completion of the digestion, 5 µl of DNase Inactivation Buffer is added, the solution incubated for 2 minutes at RT, and the samples centrifuged for 1 min in a microfuge. The RNA containing supernatant is removed and stored at $-70°$ C. In addition to the above, if the RNA is being isolated from transfected cells, the initial RNA prep is digested for 1 h at 37° C. with the restriction enzyme RsaI to cleave any contaminating plasmid DNA, the RNA reisolated using an RNeasy kit, and DNase treated with the Ambion reagents. Each sample consists of RNA isolated from 2 wells of a 6-well plate and at least three samples are isolated for each treatment/time point.

Real-time Reverse Transcription-Polymerase Chain Reaction (PCR) of RNA: Two µg of total RNA is reverse transcribed in a 100 µl total volume containing 50 mM KCl, 10 mM Tris, pH 8.3, 5.5 mM $MgCl_2$, 0.5 mM each dNTPs, 0.125 µM random hexamer, 40 units RNase Inhibitor, and 125 units MultiScribe (Applied Biosystems). In control samples the RNase inhibitor and MultiScribe are omitted. Samples are incubated for 10 min. at 25° C., 30 minutes at 48° C., and then 5 min. at 95° C. to inactivate the enzyme. Real-time PCR is then performed on 5 µl of the resulting cDNA in a total volume of 25 µl containing 12.5 µl of 2×SYBR Green PCR Master Mix (Applied Biosystems), and 0.8 µM each primer. The PCR parameters used are 2 min. at 50° C., 10 min. at 95° C., and 45 cycles of 95° C. for 15 sec. followed by 1 min. at 62° C. PCR is also performed as described on a 1/800 dilution of the cDNA with 18S primers for normalization of the samples. Relative RNA levels were calculated using the Δ Δ Ct method (Applied Biosystems).

The primers listed in Table 1 have been synthesized and successfully measured mRNA levels of gene expression in human MSCs.

TABLE 1

RT PCR Primer/Probe Sets

| Primer Name | Primer Sequence (5' to 3') | SEQ ID NO |
|---|---|---|
| Ad35LMP-1 Forward | TTCTGAGCTTCGATGTGTGTGA | 1 |
| Ad35LMP-1 Reverse | CATCATGGATTCCTTCAAGGTAGTG | 2 |
| Ad35LMP-1 Probe | 6FAM-CATCGATGCTCAGCACCCAGTCACC-TAMRA | 3 |
| hmrSMAD-1 Forward | ACCCTGTCTGAGGAGCGTGTA | 4 |
| hmrSMAD-1 Reverse | ACCAAAGCGTCCACAGCTTT | 5 |

TABLE 1-continued

RT PCR Primer/Probe Sets

| Primer Name | Primer Sequence (5' to 3') | SEQ ID NO |
|---|---|---|
| hmrSMAD-5 Forward | CACCAAGATGTGTACCATTCGAA | 6 |
| hmrSMAD-5 Reverse | GAAGAGCCCATCTGAGTAAGGA | 7 |
| hmrSMAD-6 Forward | GGATCTGTCCGATTCTACATTGTCT | 8 |
| hmrSMAD-6 Reverse | TGTCCGGTGCTCCCAGTAC | 9 |
| hmrDLX5 Forward | GGAGTTGGCCGCCTCTCTAG | 10 |
| hmrDLX5 Reverse | TGGCGAGTTACACGCCATAG | 11 |
| hmrNoggin Forward | TGCCGAGCGAGATCAAAGG | 12 |
| hmrNoggin Reverse | GTAGCGCGGCCAAAAGC | 13 |
| hBMP-2 Forward | TCCAAGAGACATGTTAGGATAAGCA | 14 |
| hBMP-2 Reverse | TCCACGTACAAAGGGTGTCTCTTAC | 15 |
| hmrSMURF-1 Forward | CCCAGAGACCTTAACAGTGTGAACT | 16 |
| hmrSMURF-1 Reverse | TTGAGTTGGCACTGGTGATTCA | 17 |
| hmrSMURF-2 Forward | TCTCGGTTGTGTTCGTCTTCTTT | 18 |
| hmrSMURF-2 Reverse | GCCTATTCGGTCTCTGGACTGAA | 19 |
| Osterix Forward | TCAGACGCCCCGACCTT | 20 |
| Osterix Reverse | ATTGGCAAGCAGTGGTCTAGAGA | 21 | siRNA treatment of cells: MSCs are transfected with Lipofectamine 2000 (Invitrogen) or Oligofectamine (Invitrogen) transfection reagent and either irrelevant siRNA or specific siRNA sequences (see Table 2). Silencing of the genes and specificity is confirmed by real-time RT-PCR analysis of specific mRNA levels and Western analysis of protein levels.

TABLE 2 siRNA sequences

| siRNA | Sense Sequence (5'-3') | SEQ ID NO: |
|---|---|---|
| SMURF1 | CCUUGCAAAGAAAGACUUCtt | 22 |
| SMURF2 | GGUGGUGGUUGAUGGAUCUtt | 23 |
| Jab-1 | GCUCAGAGUAUCGAUGAAAtt | 24 |
| LMP-1 | AGACCUUCUACUCCAAGAAtt | 25 |

Mechanistic studies using Smurf1 siRNA

1. Interaction of LMP-1 with Smurf1 not Smurf2: To confirm the specificity of the Smurf1/LMP-1 interactivity, siRNA designed to selectively target Smurf1 mRNA are utilized. Conversely, selectively inhibiting Smurf2 levels and showing that LMP-1 interaction with its candidate binding protein is not affected may also be employed. To this end, human MSCs are plated at $3 \times 10^4$ cells/well in 6-well plates, grown overnight, and treated with an irrelevant siRNA or siRNA specific for Smurf1 or Smurf2. Twenty-four hours after siRNA treatment, cells are treated with Ad5F35-LMP-1(0, 5, 10 pfu/cell) or Ad5F35-GFP. Cells are harvested 2, 4, 8, 12, 24, or 48 hr later and both cytoplasmic and nuclear proteins subjected to immunoprecipitation using LMP-1 antibody and Western analysis of co-localizing proteins using the WW domain antibody. In addition cellular total RNA and protein fractions are harvested at the same timepoints and the levels of Smurf1 and Smurf2 mRNA measured by real-time RT-PCR using primers specific for Smurf1 or Smurf2. Reduction of protein levels by siRNA is confirmed by Western blots using newly acquired antibodies thought to be specific to Smurf1 and Smurf2.

Expected Results: Reduced Smurf1 levels are expected to reduce the amount of the WW domain immunoreactive binding protein observed by Western analysis after immunoprecipitation using LMP-1 antibody compared with controls that have normal levels of Smurf1. In contrast, reduced Smurf2 levels are expected to have no effect on the amount of WW domain immunoreactive binding protein as we do not expect LMP-1 to bind Smurf2. These results would confirm that the interaction of LMP-1 is entirely with Smurf1.

2. Effects of decreasing Smurf1 on phosphorylated Smad1 and Smad5-Nuclear studies: The hypothesis is that LMP-1 binding to Smurf1 blocks Smurf1 from binding to P-Smad1 and P-Smad5, and, thus, reduces P-Smad proteasomal degradation. The expected overall effect is increased nuclear levels of P-Smad1 and P-Smad5. While it is possible that LMP-1 may have several modes of action, it is believed the interaction with Smurf1 is responsible for the osteoinductive properties of LMP-1. If the hypothesis is correct, decreasing Smurf1 levels should produce the same effect as LMP-1 to increase bone formation in vitro and responsiveness to BMP-2.

To this end human MSCs are plated at $3 \times 10^4$ cells/well in 6-well plates, grown overnight, and treated with a control irrelevant siRNA or siRNA specific for Smurf1. BMP-2 (100 ng/ml) is applied to some cultures when the siRNA is removed. Cells are harvested 4, 8, 12, 24, 36, or 48 hr later and nuclear proteins are analyzed for the presence of P-Smads by Western blot. The effectiveness of the siRNA applied to reduce the RNA and protein levels is monitored as described herein. Another group of MSCs plated as above are grown in differentiation medium for 21 days and stained with Alizarin Red to assess matrix mineralization.

Expected Results: It is expected that there will be an increase in nuclear levels of P-Smad1 and P-Smad5 in cells treated with siRNA to Smurf1 as these proteins should not be targeted for proteasomal degradation in the absence of Smurf1. It is hypothesized that the preliminary results showing increased nuclear levels of Smads in response to overexpression of LMP-1 (see example 3), was caused by LMP-1 blocking proteasomal degradation of the P-Smads. Thus, it is expected that a reduction in Smurf1 levels to mimic LMP-1 blocking of Smurf1, will result in targeting P-Smads for degradation. It is also expected that an increased responsiveness to BMP-2 in the presence of Smurf1 siRNA as evidenced by increased levels of nuclear P-Smads and increased extracellular matrix mineralization will be observed. Consequently, siRNA to Smurf1 would represent a therapeutic opportunity for matrix mineralization.

3. Effects of decreasing Smurf1 on phosphorylated Smad1 and Smad5-Cytoplasmic studies: The hypothesis is that LMP-1 binding to Smurf1 blocks Smurf1 from binding to Smad1, reduces proteasomal degradation of Smad1, and increases the responsiveness of cells to activation of the BMP-2 pathway. The expected overall effect is increased cytoplasmic levels of Smad1. While it is possible that LMP-1 may have several modes of action, it is believe the interaction with Smurf1 is important for the osteoinductive properties of LMP-1. If the hypothesis is correct, decreasing Smurf1 levels should produce a similar effect as LMP-1 in increasing responsiveness to BMP-2 as evidenced by the osteogenic response in vitro. To this end, human MSCs are plated at $3 \times 10^4$ cells/well in 6-well plates, grown overnight, and treated with a control irrelevant siRNA or siRNA specific for Smurf1. Cells are harvested 4, 8, 12, 24, 36, or 48 hr later, cytoplasmic proteins are analyzed for the presence of total Smad1 and phospho-Smad1 by Western blot and ELISA. The effectiveness of the siRNA to reduce the RNA and protein levels of Smurf1 are monitored as described herein. Another group of MSCs plated as above are grown in differentiation medium for 21 days and stained with Alizarin Red to assess matrix mineralization.

Expected Results: It is expected that treatment will result in increased cytoplasmic Smad1 in cells treated with siRNA to Smurf1 as this protein should not be targeted for proteasomal degradation in the absence of Smurf1. It has been shown, in other examples herein, that increased cytoplasmic levels of phospho-Smad1 in response to overexpression of LMP-1 and BMP-2 treatment. This result is believed to have been caused by LMP-1 blocking proteasomal degradation of Smad1. Thus, we expect reduction in Smurf1 levels to mimic LMP-1 in blocking Smurf1 targeting of Smad1 for degradation.

4. Effects of decreasing Smurf1 expression on BMP-2 responsiveness: As stated above, it is expected that directly reducing the level of Smurf1 will mimic the effect of LMP-1 overexpression. To test this hypothesis human MSCs are plated at $3 \times 10^4$ cells/well in 6-well plates, grown overnight, and treated with a control irrelevant siRNA or siRNA specific for Smurf1. BMP-2 is applied to some cultures when the siRNA is removed. After 1, 2, 4, 8, 24, 36, 48, and 72 hrs cells are harvested for analysis of total RNA or secreted, cytoplasmic and nuclear proteins including Dlx5, Smad6 and BMP-2 as previously described. Analysis by ELISA allows more accurate quantitation than can be achieved by Western blotting.

Expected Results: While not wishing to be bound by theory, it is expected that expression of Dlx5, Smad6, and BMP-2 will be increased at both the protein and mRNA levels when the Smurf1 level is reduced using specific siRNA. Cells having reduced Smurf1 levels also are expected to show an increased responsiveness to BMP-2 with regard to expression of these genes. An increased levels of expression of these genes is interpreted as a critical step for the synergistic response to BMP-2 observed in MSCs with reduced levels of Smurf1.

Biotin transfer Assay for detection of LMP-1 interacting proteins: Sulfo-SBED (Pierce), a trifunctional cross-linking agent, contains three functional groups (a photoactivatable aryl azide, a sulfonated N-hydroxy succinimide active ester with a cleavable disulfide group and a biotin moiety) and is widely used to identify interacting proteins (Neely K E, Hassan A H, Brown C E, Howe L, and Workman J L. *Mol. Cell Biol.* 2002;22:1615-25). LMP-1 is labeled using this reagent, incubated as bait with nuclear proteins and cross-linked to interacting proteins by UV (365 nm). Proteins that physically interact with LMP-1 retain the biotin group when suspended in SDS-PAGE reducing buffer. Biotin-containing target proteins are separated using neutravadin beads, detected by Western blotting with neutraviddin-HRP and the signal is developed with chemiluminescent substrate. Corresponding protein bands are in-gel digested with trypsin. Tryptic peptides are recovered, concentrated and their mass profile is analysed by MALDI-TOF at the Emory University Microchemical Facility.

LMP-1t: A 223aa osteoinductive truncated LMP-1 variant (missing LIM domains): Although LMP-1 is a LIM domain protein, it has been shown that a truncated 223aa variant of LMP-1 which lacks the LIM domains still makes bone in vitro and in vivo (Liu Y, Hair G A, Boden S D, Viggeswarapu M, and Titus L., *J.Bone Min.Res.* 2002;17:406-14). If binding to Smurf1 and activation of the BMP-2 signaling pathway is critical for LMP-1 action and induction of bone formation, then it would be expected that the truncated LMP-1 also binds Smurf1 and mimics the downstream effects of the full length protein in the presence or absence of BMP-2. To this end truncated LMP-1 (LMP-1t) fusion protein containing a Protein Transduction Domain (PTD) that readily enters cells can be designed. The suitability of this PTD for use in these and subsequent experiments is validated by showing that the PTD-LMP-1t fusion protein retains the same ability of overexpressed full length LMP-1 to compete with WW domain antibody binding, to induce increased nuclear levels of P-Smad1 and P-Smad5, and to increase expression of BMP/Smad regulated genes. Other data herein demonstrate the use of a full length TAT-LMP-1 fusion protein to enter cells readily and induce bone formation. The PTD domain proposed for use in these studies been shown to be a more effective in protein transduction than the TAT protein transduction domain used in earlier studies (Mi Z, Mai J, Lu X, and Robbins P D., *Mol.Ther.* 2000; 2:339-47).

Experimental Design: Initial studies will be required to determine a dose of PTD-LMP-1t that enhances the effect of 100 ng/ml BMP-2 on mineralization of MSCs. Human MSCs are plated at $3 \times 10^4$ cells/well in 6-well plates, grown overnight, and treated with PTD-LMP-1t (0.3-30 nM), BMP-2 (100 ng/ml) or both agents. Cells are grown in mineralizing medium as described in the Examples herein for overexpressed full length LMP-1 and the mineral stained with Alizarin Red. Two doses that synergize with BMP-2 are selected for use in subsequent studies.

Following dose selection, human MSCs are plated at $3 \times 10^4$ cells/well in 6-well plates, grown overnight, and treated with nothing or 2 doses of PTD-LMP-1t, BMP-1 (100 ng/ml) or both agents (control=PTD-βGal). After 1, 2, 4, 8, 12, 24, 36 and 48 hrs, cells are harvested and total RNA plus cytoplasmic and nuclear protein fractions are prepared. The nuclear protein fraction from the untreated sample is analyzed for the ability of purified LMP-1 protein to compete with Smurf1 antibody binding to Smurf1 on a Western blot. All protein samples are analyzed for the presence of phosphorylated Smad1 and Smad5 by Western blot using previously described appropriate antibody. All RNA samples are analyzed by real-time RT-PCR for mRNA levels of D1x5, Smad6, and BMP-2. Similarly secreted, cytoplasmic and nuclear proteins are analyzed by ELISA using commercially available antibodies to D1x5, Smad 6, and BMP-2.

Expected Results: It is expected that LMP-1t protein will enhance the osteoinductive responsiveness of MSCs to BMP-2 as seen with overexpression of the full length LMP-1 protein. It is also expected that truncated LMP-1 will bind to Smurf1 and prevent WW domain antibody binding. In addition, it is expected that there will be increased nuclear Smad levels and activation of Smad-regulated genes to exactly mimic the outcome observed with overexpression of full length LMP-1 in the presence or absence of BMP-2. This result would support the hypothesis that the LIM domains are not required for LMP-1 to induce bone formation or for LMP-1 to enhance responsiveness to BMP-2.

Smurf1-WW domain and LMP-1 interaction assay: Nuclear proteins are separated by SDS-PAGE and blotted onto nitrocellulose membrane. Protein blots are blocked with 5% milk protein and pre-incubated with purified LMP-1 protein (10 uM) or TBST buffer. Blots are incubated with Smurf antibody at 1:5000 dilution (Rabbit antibody raised to WW-domain peptide). After washes, blots are incubated with HRP-labeled Anti-rabbit second antibody. The washed blots are then incubated with ECL substrate solution and the membranes are exposed to X-ray film for signal detection.

Protein A-based immunoprecipitation assay: Protein A-agarose beads are incubated with LMP-1 antibody, washed 3 times, incubated with nuclear proteins, and washed again to remove unbound protein. Bound proteins are eluted by 2 washes in 0.1 M citric acid, pH 2.7. The eluates are neutralized with Tris base and concentrated by centricon tubes (Ambicon) prior to SDS-PAGE and Western blotting.

Pulse labeling of Smads: Cells are incubated for 1 h in the presence of ($^{35}$S)Methionine, washed extensively, incubated 30 min with Ad5F35-LMP-1 (control=Ad5F35GFP, or nothing), rinsed and returned to normal medium in the presence of BMP-2 (100 ng/ml). 1, 2, 3, 4 h after transduction, cells are harvested, nuclear fractions prepared, and radiolabeled P-Smad1 or P-Smad5 immunoprecipitated as above. Immunoprecipitates are subjected to SDS-PAGE, visualized and quantitated by autoradiography.

Modified Pulse Chase Assay for Nuclear and Cytoplasmic Analyses of Proteins.

Nuclear analysis: It has been shown herein that phosphorylated Smad1 is increased in the nucleus within 4 hrs in response to LMP-1 overexpression and is further increased at 8 hours. Possible explanations include: 1) increased gene expression of Smad1; 2) increased phosphorylation of the cytoplasmic pool of unphosphorylated Smad1 with subsequent translocation to the nucleus; and 3) reduced degradation of Smad1. The short time required for the P-Smad increase to occur does not rule out increased transcription and translation of Smad1. However, the 4 hr time frame makes it less likely that LMP-1 can be transcribed and translated and also cause increased subsequent transcription and translation of Smad1. The hypothesis for the increased nuclear level of P-Smad1 in response to LMP overexpression is that LMP-1 binds Smurf1, preventing Smurf1 from targeting P-Smad1 for proteasomal degradation. Similar accumulation of P-Smad5 is expected but has not yet been measured. The increased levels of P-Smad1 and P-Smad5 are expected to result in activation of BMP signaling, a requirement of which is that they localize in the nucleus in order to alter gene expression.

To this end, a modified pulse-chase experiment using $^{35}$S-Methionine to label newly synthesized Smad proteins and determine their rate of degradation in the presence or absence of overexpressed LMP-1 can be performed. This approach allows one to distinguish between Smad synthesis in response to LMP-1 from P-Smad accumulation in response to LMP-1.

For the pulse-chase experiment, human MSCs are plated at $3 \times 10^4$ cells/well in 6-well plates and grown overnight. $^{35}$S-Methionine ($^{35}$S-Express, NEN) are applied for 1 hr to pulse label the pool of newly synthesized proteins. Upon removal of the radiolabel and subsequent washing, cells are incubated 30 min with Ad5F35-LMP-1 (0, 5, 10 pfu/cell), Ad5F35-GFP, or nothing. BMP-2 (100 ng/ml) is applied to some cultures at the end of the transduction incubation to ensure phosphorylation of the Smad1. One, 2, 3, or 4 hr after transduction, cells are harvested and nuclear protein fractions prepared. Radiolabeled P-Smad1 or P-Smad5 are immunoprecipitated from the nuclear fraction using specific antibodies and analyzed by SDS-PAGE and fluorography.

Expected Results: Without wishing to be bound by theory, it is expected that Smad1 and Smad5 proteins will be synthesized during the labeling period and that treatment of cells with BMP-2 will result in rapid phosphorylation of some of the newly synthesized molecules. The labeled P-Smad1 and P-Smad5 would then bind Smad4 and move into the nucleus. LMP-1 and Smurf1 are predominately found in the nucleus. As overexpressed LMP-1 protein is translated it is expected to move into the nucleus and bind Smurf1. If the hypothesis is correct, this event should block subsequent degradation of P-Smad1 and P-Smad5 and result in a reduced rate of degradation compared with P-Smads in cells not overexpressing LMP-1.

Cytoplasmic analysis: Human MSCs are plated at $3 \times 10^4$ cells/well in 6-well plates, grown overnight and incubated 30 min with Ad5F35-LMP-1 (0, 5, 10 pfu/cell), Ad5F35-GFP, or nothing. To determine stability of unphosphorylated Smad1, $^{35}$S-Methionine ($^{35}$S-Express, NEN) is applied for 30 min on the next day to pulse label the pool of newly synthesized proteins and the cells subsequently washed. Cells are incubated in chase medium containing cold methionine with or without cycloheximide (10 ug/mL) for 2-3 hrs during which cells are harvested at various time points. Cells are harvested in the presence of protease inhibitors and cytoplasmic protein fractions prepared. Radiolabeled total Smad1 are immunoprecipitated from the cytoplasmic fraction using specific antibody and analyzed by SDS-PAGE and auto-fluorography. To measure stability of phospho-Smad1, similar experiments are performed in control MSCs or MSCs overexpressing LMP-1, as above. Cells are labeled with $^{32}$P-orthophosphate for 2 hr in the presence of the nuclear transport inhibitor, leptomycin B (25 uM), to assure that only decay of the labeled phospho-Smad, not the net amount of decay and transport into the nucleus is measured. $^{32}$P is removed and cells are treated for 1 hr with BMP-2 (100 ng/ml). Cytoplasmic fractions are prepared in the presence of protease and phosphatase inhibitors (to prevent loss of the $^{32}$P label). Radiolabeled $^{32}$P-Smad1 are immunoprecipitated from cytoplasmic fractions and analyzed as above.

Expected Results: Without wishing to be bound by theory, in the absence of BMP-2, it is expect that unphosphorylated Smad1 protein will be synthesized and incorporate $^{35}$S-Methionine during the labeling period. As overexpressed LMP-1 protein is translated it is expected to bind cytoplasmic Smurf1. If the hypothesis is correct, this event should block subsequent degradation of Smad1 and result in a reduced rate of degradation of Smad1 compared with cells not overexpressing LMP-1. It is expected that this block to be true of both the unphosphorylated and phosphorylated form of Smad. To determine the relative susceptibility of unphosphorylated Smad1 and phospho-Smad1 to Smurf1-mediated proteasomal degradation, comparisons of the kinetic curve for the decay of unphosphorylated Smad1 ($^{35}$S-Methionine labeled) with that of phospho-Smad1 ($^{32}$P-orthophosphate labeled) can be made. It is expected that LMP-1 will impact primarily the unphosphorylated form.

Metabolic Pulse-Chase Analysis for half life determination: To determine metabolic half-life of Smad1, MSCs are transfected with Ad5F35-LMP-1 or AD5F35-GFP and grown for 24 hr prior to metabolic labeling. Cells are washed in methionine-free medium and incubated for 15 min to deplete endogenous methionine. Cells are then incubated with the pulse-labeling medium containing [$^{35}$S]methionine (190 µCi/ml) for 30 min. After washing with chase medium (containing 150 mg/L unlabeled methionine). Cells are incubated in chase medium with or without cycloheximide (10 ug/mL) for 2-3 hr. Cells are lysed in buffer containing protease inhibitors (Sigma). Smad1 is immunoprecipitated from cytoplasmic fractions using specific antibody and analyzed by SDS-PAGE and auto-fluorography.

To determine the half life of phospho-Smad1, cells are transfected with Ad5F35-LMP-1 or AD5F35-GFP and grown for 24 hr prior to metabolic labeling. For in vivo [$^{32}$P]orthophosphate labeling, cells are pre-incubated with phosphate-free media for 1 h and exposed to 1 mCi/ml [$^{32}$P]orthophosphate for 2 h at 37° C. Leptomycin B (10 ng/ml) or Ratjadone (10 ng/ml) (Cal Biochem) is incubated with cells for 30 min to inhibit nuclear translocation of the labeled Smad1. Cells are then treated with BMP-2 (100 ng/ml) for 1 hr, lysed in buffer containing protease and phosphatase inhibitors, and the cytoplasmic fractions subjected to immunoprecipitation with phospho-Smad1 specific antibody. Immunoprecipitates are visualized by SDS-PAGE followed by auto-fluorography.

Enzyme Linked Sorbent Assay (ELSA): Purified Smurf1 is coated to individual wells of an Immulon 1B plate and the remaining surface blocked. Incubation of Smad1 and varying concentrations of competing ligand (LMP-1) and/or vice versa are performed overnight at 4° C. Using appropriate primary and enzyme linked-secondary antibodies, optical density is monitored at specific wavelengths using the BioLumin 960 microtiter plate reader or the SpectraMax M2 microtiter plate reader. The assay can be adapted several ways to suit binding partner proteins. When biotin-labeled Smad1 is assayed, streptavidin-alkaline phsophatase is used as the secondary reagent. After determining maximum binding between LMP-1/Smurf1 and Smad1/Smurf1, mutual competition curves at various concentrations will provide data for Scatchard plot analysis to obtain binding affinity, dissociation constant and number of binding sites.

Ubiquitin assay for determining extent of ubiguitination of Smad1/5 and/or LMP-1: The ELSA assay described above is modified for the ubiquitin assay as follows: Microtiter plates are coated with Smad1/5 or LMP-1 antibody and the remaining active sites are blocked by 1% BSA. Smad1/5 or LMP-1 are then captured by incubating nuclear proteins in wells. Using specific enzyme/fluorescent-linked Ubiquitin antibody and the appropriate substrate solution, the extent of ubiquitination can be assayed. The same assay can be adapted to study inhibitory effect of LMP-1 derived peptides on ubiquitination of Smads using an in vitro assay system with purified and commercially available ubiquitination assay reagents (Boston Biochemicals).

Transfection of MSCs for in vivo Bone Induction: MSCs are grown to confluence, incubated with agents being tested, trypsinized, washed 2× with PBS, suspended to 10-20 M/mL DMEM and 100 uL of the suspension applied to a sterile disc (2×5 mm) of bovine collagen. Implants are surgically placed subcutaneously on the chest of 4-6 wk athymic rats (rnu$^-$/rnu$^-$). The animals are euthanized after 4 weeks; the explants removed, fixed in 70% ethanol, and analyzed by radiography and undecalcified histology.

Mechanistic Investigations of Ubiguitination

1. Ubiquitination of Smad1 and Smad5.

It is hypothesized that the consequence of LMP-1 binding to Smurf1 is a reduction in the number of ubiquitinated Smad1 and Smad5 proteins. To this end, LMP-1 is overexpressed in hMSCs, Smad1 or Smad5 are captured on wells coated with the specific Smad antibody, and the level of ubiquitination of the Smads is quantitated by ELISA.

Human MSCs are plated at 3×10$^4$ cells/well in 6-well plates, grown overnight and treated with Ad5F35-LMP-1 (0, 5, 10 pfu/cell), or Ad5F35GFP control plasmid. After 4, 8, 12, 24, 48, and 72 hr, cells are harvested and cytoplasmic and nuclear protein fractions prepared. The cell fractions are incubated with antibody to Smad1 or Smad5 in a 96 well plate coated with the antibody. After washing to remove nuclear proteins not associated with Smad1 or Smad5, fluorescence tagged-ubiquitin antibody is applied and the fluorescence is detected using a Biolumin 960 microtiter plate reader. Use of the fluorescent tagged antibody increases sensitivity and allows quantitation of the low level of ubiquitin expected to be present in the sample. To validate the ELISA results, another aliquot of the cell fractions undergoes immunoprecipitation using anti-Smad1 or anti-Smad5 antibody and the precipitated proteins are analyzed by Western blotting using antibody to ubiquitin as well as antibody to Smad1 or Smad5.

Expected Results: It is expected that the Western analysis will show a smear with both the ubiquitin and Smad1 or Smad5 antibodies representing Smads conjugated with ubiquitin chains of various lengths. The Smad1 antibody is expected to capture only Smad1 and the Smad5 antibody is expected to capture only Smad5. Free ubiquitin is removed during the ELISA washes. Additional ubiquitinated proteins are not expected to be observed. Compared with untreated or GFP treated cells, it is expected that lower levels of Smad ubiquitination will occur when LMP-1 is overexpressed due to interruption of Smurf1 function. It should be noted that this method will not distinguish whether decreased ubiquitination is due to variation in the number of ubiquitin subunits linked to Smads or fewer Smad molecules that are conjugated to ubiquitin chains. Examination of Western blots performed for Smad1 or Smad5 and ubiquitin may resolve this issue.

2. Effects of LMP-1 siRNA Treatment on Ubiquitination.

Upon demonstration that forced expression of LMP-1 can alter the level of ubiquitinated Smad1 and Smad5, reduction of endogenous levels of LMP-1 using siRNA would be expected to increase the rate of degradation of those Smad proteins. Other examples herein have shown that siRNA targeting LMP-1 are effective at reducing LMP-1 levels. Using these siRNA, studies investigating the relationship between LMP-1 and ubiquitination of Smads can be performed. To show that application of siRNA to reduce the endogenous LMP-1 levels results in increased levels of ubiquitinated Smad1/5 human MSCs are plated at $3 \times 10^4$ cells/well in 6-well plates, grown overnight, and treated with a control irrelevant siRNA or specific LMP-1 siRNA. Cells are harvested 4, 8, 12, 24, 48, or 72 hr later and both cytoplasmic and nuclear fractions prepared. The cell fractions are incubated with antibody to Smad1 or Smad5 in a 96 well plate coated with the antibody. After washing to remove nuclear proteins not associated with Smad1 or Smad5, fluorescence tagged-ubiquitin antibody are applied and the fluorescence detected as in other examples herein. This approach allows quantitation of the low level of ubiquitin that is expected to be present in the sample.

Expected Results: It is expected that reduced levels of endogenous LMP-1 will increase ubiquitination of both Smad1 and Smad5. We would interpret this as being due to greater availability of Smurf1 molecules for Smad binding.

3. Ubiquitination of Smad1 by Smurf1

It is believed that LMP-1 prevents Smurf1 interaction with Smad1, resulting in decreased ubiquitination of Smad1. Reduced ubiquitination is therefore expected to result in reduced proteasomal degradation of Smad1 protein. To demonstrate that the interaction of LMP-1 with Smurf1 inhibits ubiquitination of Smad1, in vitro ubiquitination assays are performed.

To this end, biotin labeled Smad1 is prepared by the TNT-coupled reticulocyte lysate system (Promega) and impurities removed by capturing Smad1 using neutravidin-linked resin. Smad1 is mixed with a mixture of purified E1 and E2 ligases and incubated with the Smad ubiquitin E3 ligase, Smurf1, in the presence or absence of recombinant LMP-1 protein. The reaction mixture also contains ubiquitin and the creatine kinase-ATP generating system. The reaction mixture is analyzed by SDS-PAGE and Western blots using specific antibody to ubiquitin or Strepavidin-HRP (to detect Biotin-Smad1).

Extpected Results: It is expected that there will exist a baseline ubiquitination of Smad1 by Smurf1 under the conditions of the reaction. Further, it is expect that addition of LMP-1 will inhibit this reaction. This will identify Smurf1 as an E3 ligase with which LMP-1 interacts to reduce Smurf1-induced ubiquitination of Smad1.

4. Effects of Smurf1 siRNA Treatment on Ubiquitination.

It is possible that LMP-1 binding to Smurf1 leads to its own ubiquitination and subsequent proteasomal degradation. However, there are examples of proteins that bind E3 ligases without being degraded (Murillas R, Simms K S Hatakeyama S, Weissman A M, and Kuehn M R. *J.Biol.Chem.* 2002; 277:2897-907). Our empirical data that relatively small amounts of LMP-1 alone profoundly activate the BMP-2 pathway suggest that LMP-1 itself may not be targeted for proteasomal degradation by Smurf1, but rather occupy the Smad1/5 binding site, preventing Smad1/5 targeting and degradation. To determine whether reducing the levels of Smurf1 results in reduced LMP-1 ubiquitination and increased levels of endogenous LMP-1, human MSCs are plated at $3 \times 10^4$ cells/well in 6-well plates, grown overnight, and Smurf1 or control siRNA applied. Cells are harvested 4, 8, 12, 24, 48, or 72 hr later and both cytoplasmic and nuclear fractions prepared. The cell fractions are incubated with antibody to LMP-1 in a 96 well plate coated with the antibody. After washing to remove nuclear proteins not associated with LMP-1, fluorescence-tagged ubiquitin antibody is applied and fluorescence detected as above. This approach allows quantitation of the level of ubiquitin in the sample. In other wells, captured LMP-1 levels is quantitated by applying fluorescence tagged-LMP-1 antibody. To validate that the ELISA measurements are specific to ubiquitinated LMP-1, another aliquot of the cell fractions undergoes immunoprecipitation using anti-LMP-1 antibody and the precipitated proteins are analyzed by Western blotting using antibody to ubiquitin as well as antibody to LMP-1.

Expected Results: It is not believed that LMP-1 undergoes ubiquitination by Smurf1. Thus, it is expected that decreased levels of Smurf1 will not change the level of ubiquitinated LMP-1 compared with cells with normal levels of Smurf1. Further it is predicted that reduced levels of Smurf1 will have no effect on the level of LMP-1 protein within cells. In concluding that Smurf1 does not target LMP-1 for proteasomal degradation, it is suggested that LMP-1 binds Smurf1 at the site that also binds Smad1 or Smad5, blocking Smad ubiquitination and targeting for proteasomal degradation. Therefore, this interruption of Smurf1 function would be a primary mechanism by which LMP-1 enhances signaling of the BMP-2 pathway.

5. Ubiquitination Reaction in vitro:

Purified Smad1 (100 ng) is buffer-exchanged to ubiquitination buffer (50 uM Tris-HCl pH 7.8, 5 mM $MgCl_2$, 0.5 mM dithiothreitol (DTT), 2 mM NaF, and 3 μM okadaic acid). Smad1 is then combined with a mixture of purified E1 and E2 enzymes and incubated with Smurf1 (E3 ligase) in the presence or absence of recombinant LMP-1 or LMP-2 protein. The reaction mixture also contains 2 mM ATP, ubiquitin (150 μM), ubiquitin aldehyde (5 μM), and creatine kinase-ATP generating system (Boston Biochem). The ubiquitin aldehyde is included to prevent hydrolysis of polyubiquitin chains. The reaction mixture (40 μL) is incubated 4 hr at 37° C. Aliquots at various time points are taken for SDS-PAGE and western blotting using specific antibody for Smad1 and/or ubiquitin.

Mechanistic Studies of the BMP-2 Receptor (BMPR1A)

1. Smurf1/Smad6 Complexes

One hypothesis by which LMP-1 enhances cellular responsiveness to BMP-2 is by increasing the BMPR1A (ALK3) level in the plasma membrane. Smurf1 has been shown to regulate the proteasomal degradation of BMP-2 receptors through its interaction with I-Smads (Murakami, G., Watabe, T., Takaoka, K., Miyazono, K., and Imamura, T., *Mol. Biol. Cell.* 2003, 14:2809-2817, 2003. It is suggested that I-Smad/Smurf1 complexes form in the nucleus and translocate to the plasma membrane where I-Smad binding to the receptor occurs. Once bound to the receptor complex, Smurf1 ubiquitinates the I-Smad and BMPR1A receptor, targeting them for proteasomal degradation (Ebisawa, T., Fukuchi, M., Murakami, G., Chiba, T., Tanaka, K., Imamura, T., and Miyazono, K., J. Biol. Chem. 2001, 276:12477-12480; Izzi, L. and Attisano, L., Oncogene. 2004, 23:2071-2078). To test the hypothesis that LMP-1/Smurf1 interaction prevents formation of Smurf1/I-Smad (Smad6) complexes, recombinant Smurf1, LMP-1 and biotin-Smad6 are purified and tested in an ELSA binding competition assay. The assay is described fully herein. Briefly, wells of a 96-well plate are coated with Smurf1 protein and preincubated in the presence or absence of different amounts of LMP-1. After washing, biotin-Smad6 is incubated with the Smurf1 complexes and binding detected using strepavadin-alkaline phosphatase. Absorbance is monitored at 405 nm using the SpectraMax M2 microplate reader.

Expected Results: It is expected that, in the absence of LMP-1, Smurf1/Smad6 complexes will be detected. In the presence of increasing concentrations of LMP-1, decreasing amounts of Smurf1/Smad6 complex are expected to be formed until complete inhibition of Smad6 binding is achieved.

2. Smurf-1 Mediated Export of Smad6 from the Nucleus.

In the absence of receptor activation, I-Smads have been shown to primarily reside in the nucleus, but activation of the receptor results in translocation of I-Smads to the cytoplasm (Itoh, F., Asao, H., Sugamura, K., Heldin, C. H., ten Dijke, P., and Itoh, S., *EMBO J.* 2001, 20:4132-4142; Nakayama, T., Gardner, H., Berg, L. K., and Christian, J. L., *Genes Cells,* 1998, 3:387-394). It has been suggested that the export of Smad6 from the nucleus is facilitated by Smurf1 (Izzi, L. and Attisano, L., *Oncogene* 2004, 23:2071-2078); Suzuki, C., Murakami, G., Fukuchi, M., Shimanuki, T., Shikauchi, Y., Imamura, T., and Miyazono, K., *J. Biol. Chem.,* 2002, 277: 39919-39925). Since the hypothesis is that LMP-1 binds Smurf1 in the same site as Smurf1 binds Smads, it is expected that the consequence of LMP-1/Smurf1 interaction will be that less Smad6 moves to the cytoplasmic compartment as a result of BMP-2 activation of its receptor. To this end, Flag-Smad6 is overexpressed to show that LMP-1 blocks the BMP-2-mediated translocation of Smad6 into the cytoplasm. Overexpressed Flag-Smad6 is used rather than endogenous Smad6 because of the specificity of the Flag antibody and cross-reactivity of Smad6 antibodies with other Smads.

Experimental Design: Human MSCs are plated at $3 \times 10^4$ cells/well in 6-well plates, grown overnight, and transfected with 3 ug empty vector or plasmid containing Flag-Smad6. After the transfection, cells are allowed to recover for 1 hr prior to transduction with Ad5F35-LMP-1 or Ad5F35-GFP (0, 5, 10 pfu/cell). Twenty-four hours after the transduction is complete, BMP-2 (100 ng/mL) is applied to the cells. Cells are harvested 1, 2, 4, 8, and 12 hrs after BMP-2 treatment is initiated and cytoplasmic and nuclear fractions prepared. Fractions are subjected to SDS-PAGE and Western analysis using Flag specific antibody.

Expected Results: An increase in Smad6 in the cytoplasm upon BMP-2 receptor activation is expected. However, in cells overexpressing LMP-1 this increase is not expected. These results would suggest LMP-1/Smurf1 complexes form and interrupt the formation of Smurf1/Smad6 complexes that move Smad6 into the cytoplasm. It is believed that disrupting movement of Smad6 from the nucleus to the cytoplasm is a critical first step that is required for LMP-1 disruption of Smurf1/Smad6-mediated proteasomal degradation of BMPR1A.

This finding would also be important in elucidation of the overall mechanism of LMP-1 enhancement of responsiveness of MSCs to BMP-2. If LMP-1 blocks Smurf1 from interacting with Smad6, it would seem that the free Smad6 would still be available in the cytoplasm to oppose the other effects of LMP-1 on BMP action. However, it is expected that Smad6 is not exported from the nucleus to the cytoplasm in the presence of LMP-1. Thus, it is important to demonstrate that Smad6 levels do not increase in the cytoplasm.

3. LMP-1 Effects on the Amount of BMPR1A in the Plasma Membrane of MSCs.

It is believed that the consequence of reducing Smurf1/Smad6 interaction will be an increase in the level of BMPR1A in the plasma membrane. Results disclosed herein suggest that BMP-2 increases BMPR1A in cells overexpressing LMP-1 more than in control cells. This finding would represent the sum of BMP-2 action to increase receptor number and the action of LMP-1 to reduce proteasomal degradation of the receptor. This experiment allows for the elucidation of the effect of LMP-1 alone on this increase in receptor. Increasing receptor number is an extremely powerful mechanism for increasing the responsiveness of MSCs to BMP-2.

Experimental Design: Human MSCs are plated at $3 \times 10^4$ cells/well in 6-well plates, grown overnight, and treated with Ad5F35-LMP-1 or Ad5F35-GFP (0, 5, 10 pfu/cell). After 1, 2, 4, 8, 12, 24 and 48 hrs, cells are harvested and plasma membrane enriched fractions prepared. Fractions are subjected to SDS-PAGE and Western analysis using BMPR1A specific antibody.

Expected Results: Increased levels of BMPR1A in the plasma membranes of MSCs overexpressing LMP-1 are expected. This increase would likely be due to decreased proteasomal degradation of the receptor by Smurf1/Smad6 complexes in the presence of increased LMP-1. Consequently, this finding would represent a second significant mechanism by which LMP-1 enhances the osteoinductive efficacy of BMP in MSCs.

4. Effects of LMP-1 on Ubiguitinated BMPR1A.

It is hypothesized that the receptor increase shown above would be due to decreased ubiquitination and proteasomal degradation because of reduced interaction with the Smurf1/Smad6 complex. To test that hypothesis, the levels of ubiquitinated BMPR1A are measured. Past experience suggests that detection of ubiquitinated receptors by ELISA will be difficult because receptor proteins do not adhere to plastic consistently. Thus, Western blot analysis is used to determine changes in the level of ubiquitination.

Experimental Design: Human MSCs are plated at $3 \times 10^4$ cells/well in 6-well plates, grown overnight and treated with Ad5F35-LMP-1 (0, 5, 10 pfu/cell), or Ad5F35GFP control plasmid. After 4, 8, 12, 24, and 48 hr, cells are harvested and plasma membrane enriched fractions prepared. BMPR1A are immunoprecipitated from the cell fractions using beads coated with specific antibody. The beads are washed and the precipitated proteins are analyzed by Western blotting using antibody to ubiquitin as well as antibody to BMPR1A.

Expected Results: Western analysis is expected to show a smear with both the ubiquitin and BMPR1A antibodies representing BMPR1A conjugated with ubiquitin chains of various lengths. Additional ubiquitinated proteins are not expected. Compared with untreated or GFP treated cells, lower levels of BMPR1A ubiquitination are expected when LMP-1 is overexpressed due to interruption of Smurf1/

Smad6 function. It should be noted that this method may not quantitatively distinguish whether decreased ubiquitination is due to variation in the number of ubiquitin subunits linked to BMPR1A or fewer BMPR1A molecules that are conjugated to ubiquitin chains. Nevertheless, a comparison between treatments can be made, reflecting different amounts of ubiquitinated BMPR1A among various treatments.

If ubiquitinated BMPR1A is not detectable it is likely to be caused by rapid degradation of the ubiquitinated receptor. In that case, the experiment would be performed in the presence of the proteasome inhibitor, lactacystin, to accumulate ubiquitinated BMPR1A for detection in Western blots.

This method may not be sensitive enough to detect the low levels of ubiquitinated BMPR1A that are present, but it is felt that ELISAs are likely to be inconsistent using hydrophobic receptor proteins. Therefore, if there are not enough ubiquitinated receptors, Smurf1 and Smad6 can be overexpressed in the presence or absence of LMP-1 and the experiment can be repeated. Alternatively, if there are too few receptors to detect by Western analysis, Flag-BMPR1A can be overexpressed the experiment repeated using Flag antibody to immunoprecipitate proteins for Western blot analysis.

Mechanistic Investigations of LMP-1 and Jab1

1. Effect on BMP-2 Responsiveness on Interrupting Jab1-mediated Proteasomal Degradation of Smad4

One hypothesis is that LMP-1 enhances responsiveness of MSCs to BMP-2 by binding to Jab1 and preventing Jab1-induced proteasomal degradation of Smad4. Jab1 is an adapter protein that targets Smad4 for ubiquitination and regulates the rate of Smad4 degradation, an important role in controlling the cytoplasmic levels of Smad4. Smad4 is required for translocation of phospho-Smad1/5 into the nucleus and has been shown to be critical in regulating the responsiveness of cells to BMP-2 (Hata, A., Lagna, G., Massague, J., and Hemmati-Brivanlou, A., *Genes Dev.* 1998, 12:186-197; Moren, A., Hellman, U., Inada, Y., Imamura, T., Heldin, C. H., and Moustakas, A., *J. Biol. Chem.* 2003, 278: 33571-33582).

Other studies herein have demonstrated that LMP-1 overexpression increases Smad4 levels. Thus, reduction of endogenous levels of LMP-1 using siRNA would be expected to decrease Smad4. It is hypothesized that this decrease would be caused by increased proteasomal degradation of Smad4 and that it would not occur in the presence of the proteasomal inhibitor, lactacystin. More specific evidence that reducing LMP-1 enhances proteasomal degradation of Smad4 requires demonstration of increased ubiquitination of Smad4 protein when LMP-1 levels are reduced. To this end, studies are performed that demonstrate that reduction of endogenous LMP-1 by siRNA increases proteasomal degradation of Smad4.

Experimental Design: Human MSCs are plated at $3\times10^4$ cells/well in 6-well plates, grown overnight, and treated with a control irrelevant siRNA or specific LMP-1 siRNA in the presence or absence of lactacystin. Cells are harvested 4, 8, 12, 24, 48, or 72 hr later and total RNA or cytoplasmic protein fractions prepared. An aliquot of the protein fraction is analyzed by Western blot using antibodies to Smad4. Another aliquot of cytoplasmic proteins is incubated with antibody to Smad4 in a 96 well plate coated with the antibody. After washing to remove proteins not associated with Smad4, fluorescence tagged-ubiquitin antibody is applied and the fluorescence detected using a SpectraMax M2 combined fluorescence and absorbance microplate reader. This approach allows quantitation of the low level of ubiquitin that is expected to be present in the sample.

Expected Results: An increase in ubiquitination would likely be due to greater availability of functional Jab1 molecules for Smad4 binding. Taken together these findings would suggest that LMP-1 could block proteasomal degradation of Smad4. A less likely alternative is that the LMP-1/Jab1 interaction results in increased sumoylation of Smad4 which is an alternative mechanism of enhanced stability of Smad4 (Lee, P. S., Chang, C., Liu, D., and Derynck, R., *J. Biol. Chem.* 2003, 278:27853-27863). Another possibility is that the interaction of Jab1 with Smad7, a TGF-β inhibitory Smad, could augment the BMP-2 responsiveness portion of these experiments by decreasing availability of TGF-β phospho-R-Smads (Kim, B. C., Lee, H. J., Park, S. H., Lee, S. R., Karpova, T. S., McNally, J. G., Felici, A., Lee, D. K., and Kim, S. J., *Mol. Cell Biol.* 2004, 24:2251-2262).

2. Investigation of the Requirement of Jab1 for LMP-1 Induced Effects.

Studies herein have demonstrated a direct interaction between Jab1 and LMP-1 and it is well known that ectopic expression of Jab1 in certain cell lines can decrease Smad4 steady-state levels (Wan, M., Cao, X., Wu, Y., Bai, S., Wu, L., Shi, X., Wang, N., and Cao, X., *EMBO Rep.* 2002, 3:171-176).

Experimental Design: To demonstrate that Jab1 is required for LMP-1-induced effects on Smad4, human MSCs are plated at $3\times10^4$ cells/well in 6-well plates, grown overnight, and treated with a control irrelevant siRNA or specific Jab1 siRNA in the presence or absence of rhBMP-2 (100 ng/ml). Cells are harvested 4, 8, 12, 24, 48, or 72 hr later and total RNA or cytoplasmic and nuclear protein fractions prepared. Cell fractions are analyzed by Western blots using specific antibodies to Smad4 and phospho-Smad1. The efficacy of Jab1-specific siRNA to lower Jab1 levels are assessed by real time RT-PCR and Western analysis using Jab-1 specific antibody.

Expected Results: It is expected that reducing endogenous Jab1 will increase cytoplasmic Smad4 levels as has been shown herein with overexpression of LMP-1. Further, in cells treated with rhBMP-2, it is expected that reducing Jab1 will increase nuclear phospho-Smad1, as a result of the increased pool of cytoplasmic Smad4 available to translocate activated R-Smads to the nucleus. These results would indicate that Jab1 regulates responsiveness of BMP-2 in MSCs by regulating Smad4 proteasomal degradation. This would complement work by others demonstrating this relationship in transformed cell lines or cancer cells (Wan, M., Cao, X., Wu, Y., Bai, S., Wu, L., Shi, X., Wang, N., and Cao, X., *EMBO Rep.*, 2002 3:171-176).

3. Effect of LMP-1 on Jab1-mediated Decrease in Smad4

If decreasing endogenous Jab1 as above increases Smad4, mimicking the effect of LMP, it would be expected that overexpression of Jab1 would decrease cytoplasmic Smad4. Further, if LMP-1 exerts its effects on Smad4 levels by decreasing its Jab1-induced degradation, then overexpressed LMP-1 should reverse the effect of overexpressing Jab1.

Experimental Design: To test this hypothesis, human MSCs are plated at $3\times10^4$ cells/well in 6-well plates, grown overnight, and transfected with plasmid containing Jab1 or empty vector. After a 1 hour recovery period cells are transduced with Ad5F35-LMP-1 or Ad5F35-GFP (0, 5, 10, 25, 50, 100 pfu/cell). After 1, 2, 4, 8, 12, 24 and 48 hr, cells are harvested and cytoplasmic fractions prepared. Cytoplasmic fractions are analyzed for Smad4 and Jab1 by Western blot using specific Smad4 or Jab1 antibody.

Expected Results: It is expected that increasing Jab1 levels will result in decreased cytoplasmic Smad4 in the absence of overexpressed LMP-1. If the hypothesis that LMP-1 increases Smad4 through its interaction with Jab1 is correct, then overexpression of LMP-1 should overcome the effect of Jab1 overexpression. These results would confirm that LMP-1 blocks Jab1-induced proteasomal degradation of Smad4. The LMP-1/Jab1 interaction may either prevent Jab1 binding to Smad4 or block the ability of Jab1 to serve as an adapter protein that increases targeting of Smad4 for ubiquitination and subsequent proteasomal degradation. This question could be resolved by competition binding studies. In either case, however, the overall effect of a LMP-1/Jab1 interaction would be to increase Smad4 levels.

If LMP-1 overexpression fails to overcome the effect of Jab1 overexpression on Smad4 levels there may be insufficient LMP-1 levels to overcome the high level of Jab1 expression. To resolve this issue, the experiment would be repeated with higher doses of Ad5F35-LMP-1. While it has been demonstrated in other studies herein that the doses of Ad5F35-LMP-1 that are applied synergize with BMP-2 in MSCs, the doses to overcome the effect of Jab1 overexpression have not been tested. If toxicity is observed as a result of "double overexpression," a recombinant LMP-1 fusion protein (TAT-LMP-1) could be used instead of Ad5F35-LMP-1 as demonstrated in other studies herein.

4. Enhancement of Physiologically Relevant Markers of BMP-2 Responsiveness

To investigate the combined effect on BMP-2 responsiveness, a series of experiments are performed to demonstrate the effect of LMP-1 overexpression. First, a Smad-responsive luciferase reporter construct (9×GCCG) is first used to determine the effect of LMP-1 overexpression on luciferase activity. Next, expression of the BMP-2 regulated gene, Dlx5 is measured. Other studies disclosed herein suggest Dlx5 is important for the synergistic effects of LMP-1 and BMP-2 to induce the osteoblast phenotype in MSCs.

Experimental Design: Human MSCs are plated at 3×10$^4$ cells/well in 6-well plates, grown overnight transfected with 3 ug 9×GCCG/luciferase reporter construct and treated with Ad5F35-LMP-1 (0, 5, 10 pfu/cell), (control=Ad5F35GFP), BMP-2 (100 ng/mL), or both. After 4, 8, 12, 24, 48, and 72 hr, cells are harvested and luciferase activity determined (Promega).

A second set of experiments is performed without transfection of luciferase reporter in which RNA is harvested at the same time points for detection of D1×5 expression using real time RT-PCR.

Expected Results: LMP-1 overexpression is expected to greatly enhance the reporter construct activity in response to BMP-2. In addition, a smaller increase in activity is expected with either LMP-1 alone or BMP-2 alone. Since LMP-1 increases the pool of R-Smads and the Co-Smad, this could result in some increase in activated R-Smad/CoSmad complexes in the nucleus (as suggested by other data herein). However it is expected that the largest effect observed in enhancing BMP-2 efficacy would be due to the effect of LMP-1 to reduce degradation of many important proteins in the BMP-2 signaling cascade.

LMP-1 is further expected to enhance the BMP-2 increase in the Dlx5 gene expression as suggested by results disclosed herein. Therefore, if the results are as expected, one mechanisms by which LMP-1 increases responsiveness to BMP-2 may likely involve reduced degradation of BMPR1A, R-Smads, and Co-Smad4.

Alkaline Phosphatase mRNA levels: Alkaline phosphatase activity is an early marker of the osteoblast phenotype. Human MSCs treated with Ad5/35LMP-1 (0, 1, 5, 10 pfu/cell) with and without BMP-2 (100 ng/ml) are harvested for RNA at day 8. Cells are washed with PBS once and cell lysates are prepared by sonication. RNA is isolated and alkaline phosphatase mRNA was quantified by RT-PCR with the alkaline phosphatase specific primers. Alkaline phosphatase activity is measured using p-nitrophenyl phosphate as substrate where nzyme activity is expressed as p-nitrophenol produced (nmoles/ml). Data is normalized to 18S.

Osterix Message in Human MSCs: Osterix is a novel zinc finger-containing transcription factor required for osteoblast differentiation and bone formation. Human MSCs are treated with Ad5/35LMP-1 with and without BMP-2 and harvested for RNA at day 8. RNA is isolated and osterix MRNA is quantified by RT-PCR with the osterix primers. Data is normalized to 18S.

Bacterial Strains and Cloning of cDNAs in bacterial expression vectors: All cloning methods are performed according to standard protocols. *Escherichia coli* XL 1 blue and BL 21-codon plus (DE3)-RP (Stratagene) hosts are maintained on LB agar plates and grown at 37° C. in the presence of ampicillin at 100 mg/L. LMP-1, LMP-1t, LMP-2, LMP-3, Smad1 and Smad5 cDNAs were cloned into TAT-HA vector. LMP-1 mutants were generated using the primers in Table 3.

TABLE 3

Primers for LMP-1 mutants

| LMP primer name | Primer Sequence (5'-3') | SEQ ID NO: |
|---|---|---|
| hLMP1 Mutant A forward primer | cgccccgccgcggacgcagcacggtacacctttgcac | 26 |
| hLMP1 Mutant A reverse primer | gtgcaaaggtgtaccgtgctgcgtccgcggcggggcg | 27 |
| hLMP1 Mutant B forward primer | ggcccggcccttgggcggcagcagcagctgacagcgccccgcaac | 28 |
| hLMP1 Mutant B reverse primer | gttgcggggcgctgtcagctgctgctgccgccccaaagggccgggcc | 29 |

Smurf1 cDNA is cloned into pTrcHis vector (Invitrogen). For generation of Smurf1Δ WW2 mutant, the primers in Table 4 are used. Mutagenesis is performed with Quikchange site-directed mutagenesis kit (Stratagene).

TABLE 4

Primers for Smurf1 mutants

| Smurf1 primer name | Primer Sequence (5'-3') | SEQ ID NO: |
|---|---|---|
| hSMURF1 WW2 forward primer | gtgtgaactgtgatgaacttaatcaccagtgccaactc | 30 |
| hSMURF1 WW2 reverse primer | gagttggcactggtgattaagttcatcacagttcacac | 31 |

Expression and purification of recombinant proteins: Bacterial cultures are grown at 37° C. until O.D. 600 reaches 0.8. IPTG is added to 200 µM and the culture grown for another 8 hr. Cells are harvested and pellets are suspended in ice-cold lysis buffer (20 mM phosphate buffer, pH 7.0 containing 50 mM Tris-HCl, pH 7.5 and 0.5 M NaCl). The uniform cell suspension is sonicated (Sonicator, Model W-385, Heat systems-Ultrasonics, Inc.) using 4×15 sec bursts at minimum power-output settings in ice with a 2 min interval between each burst. The lysate is centrifuged at 10,000 g at 4° C. and the supernatant applied to Sephacryl S-100/S-200 columns (HiPrep 16×60) using AKTA FPLC system with Unicorn 4.0 software (Amersham Pharmacia Biotech) at a flow rate of 1 ml/min. Fractions (2-4 ml) are collected immediately after the void volume (35 ml). Aliquots, from each fraction are assayed by slot blotting, SDS-PAGE and western blotting. The fractions, identified by western blots are pooled, dialyzed against 20 mM phosphate buffer, pH 7.5 containing NaCl (50 mM) and imidazole (20 mM) and applied to Ni++ affinity resin (Probond, Invitrogen) previously equilibrated with 4×10 ml of buffer. Non-specific proteins are washed off the column with 3×10 ml of 20 mM phosphate buffer, pH 6.0 containing NaCl (50 mM) and imidazole (20 mM). Affinity-bound proteins are eluted using 3×10 ml washes with 20 mM phosphate buffer, pH 4.0 containing NaCl (50 mM). Fractions containing the desired protein are pooled (based on western blot) and then concentrated and de-salted using the centriprep devices (Amicon). Proteins are quantitated using BioRad protein assay reagent. The yield of recombinant protein is routinely 0.5 to 1 mg of pure protein from every 2-liter culture.

Biotinylation of protein ligands: Purified protein ligands are prepared at 10 mg/ml in 50 mM sodium borate buffer, pH 8.5; 0.5 M NaCl. Various amounts of sulfo-NHS-biotin (100 mM stock in DMSO) are mixed with protein ligand to achieve a molar ratio of Sulfo-NHS-biotin/protein ligand of 10.0 in a 100 µl reaction volume. After 2 hr on ice with occasional shaking the reaction is terminated with the addition of lysine to a final concentration of 20 mM. The unreacted free biotin is removed by gel filtration and the concentrated labeled ligand stored at −200° C. until use. Labeled or unlabeled LMP-1, Smad1, Smurf1 and Smad5 are prepared by using TnT coupled in vitro transcription/translation system (Promega).

Slot-blot assay: 20 ul of purified Smurf1 (50 µg/ml) is blotted onto nitrocellulose in slot blot wells and the wells are blocked with 0.5% Tween 20 in TBST for 30 min. Biotinylated ligand (LMP-1, LMP-2, LMP-3, Smad1 or Smad5) is mixed with varying concentrations of competing proteins or peptides and incubated in slot blot wells with Smurf1 for 90 min. Wells are washed and the blots were blocked with TBST containing 0.5% Tween 20. The blots are then incubated with HRP-labeled avidin for 1 hr. After washes the blots are incubated with ECL substrate solution and the membranes are exposed to X-ray film for signal detection.

Preparation of peptides having a protein transduction domain (PTD): Peptides are synthesized with a protein transduction domain (PTD) at the c-terminal end, (rrqrrtsklmkr, herein incorporated as SEQ ID NO: 32) according to Mi Z, et. al.; Mol. Ther. 2000;2:339-47.

Osteogenic differentiation of hMSCs: hMSCs at passage 4 are seeded at $3\times10^4$ cells/well in a 6-well plate. The next day, the cells are infected with Ad35LMP-1 (1-10 pfu/cell) and incubated with and without BMP-2 (100 ng/ml). The medium is replaced every 3-4 days and deposition of mineral observed after 2 weeks. To assess mineralization, cultures are washed with PBS and fixed in a solution of ice-cold 70% ethanol for 2-3 hours. Cultures are rinsed with water and stained for 10 minutes with 1 ml of 40 mM Alizarin red (pH 4.1). Cultures are rinsed 2-3 times with PBS to reduce non-specific staining, air dried and photographed.

Ectopic Bone Formation Experiments

Ninety 4-6 week old male athymic rats ($rnu^-/rnu^-$, Harlan; housed in sterile cages (2 rats/cage) and observed daily) are used to test LMP-1-mimetic compounds for their ability to enhance responsiveness of MSCs treated with sub-optimal doses of BMP-2 (2.5 ug/ml) to induce bone formation in the rat model of ectopic bone formation. Athymic rats are used as they have no immune response to implanted foreign materials. After approval by the IACUC, 4-6 week old rats are anesthetized using 1.5% Isoflurane and the chest scrubbed with Chlorohexiderm spray. This method is consistent with the recommendations of the Panel on Euthansia of the AVMA is selected because it is a rapid and painless method of euthanasia for rats.

Chest implants: The surgical area is draped using sterile drapes with a hole cut to allow access to the surgical area. Surgery is performed on a draped circulating water heating pad. A 1 cm skin incision is made in 4 locations on the chest, the skin separated from the muscle by blunt dissection and the discs loaded with BMP-2 +cells positioned in separate pockets. Incisions are closed using resorbable sutures. Rats typcially survive 4 weeks after which they are euthanized using canister $CO_2$ consistent with the recommendation of the AVMA.

Controls: Because of the narrow efficacious dose range for LMP-1 it is necessary to test multiple doses of each compound and to include positive control (i.e.TAT-LMP-1) and negative (i.e. cells alone or cells+BMP-2 only) controls. The positive control chosen should not induce bone formation when given at the chosen dose without BMP-2. Each dose or control is tested on multiple sites and there are multiple sites/rat. If compounds are postive, more testing can be performed.

Anesthesia: Anesthesia is adminsitered using 1.5% isoflurane prior to the surgical procedure. Prior to making incisions Bupivicaine 0.1-0.3 ml is given by subcutaneous or intramuscular injection around the surgical site. Buprenorphine (Buprenex) (0.05 mg/100 g) is injected subcutaneously immediately post-operatively and every 8 hrs for 3 days post-op to relieve pain.

Ectopic Experiments of Smurf1 Binding Peptides that Induce Bone Formation in vivo With the main hypothesis that interaction of LMP-1 with Smurf1 results in increased BMP-2 signaling activity and bone formation, it is expected that peptides that bind Smurf1 and activate the BMP/Smad signaling pathway in vitro can also induce bone in vivo in the rat model of ectopic bone formation. Once peptides that induce bone formation have been identified, these peptides are tested in combination with low doses of BMP-2 to determine whether there are synergistic effects (as seen in vitro) that might lower the required dose of either agent. To evaluate potential synergy, identified herein is a dose of BMP-2 (2.5 ug) that induces bone formation in only 50% of the implants and a lower dose (1 ug) that consistently fails to induce bone formation in the rat ectopic model. These doses are known as the "suboptimal doses."

Experimental Design: In these studies, multiple doses of each of several peptides are studied. The positive control are MSCs treated with Ad5F35-LMP-1 (5 pfu/cell). MSCs (1-2M) are mixed with appropriate doses of peptides in a 100 uL total volume and placed on a collagen disc. The disc is implanted subcutaneously on the chest of athymic rats and explanted after 4 weeks. Bone formation is evaluated by palpation, x-ray and semi-quantitative scoring of non-decalcified histologic sections (Edwards J T Diegmann M H and Scarborough N L. *Clin.Orthop.* 1998;219-28). It has been previously found that 1-2 million cells transduced with TAT-LMP can induce bone formation in this model, although not consistently. Hence, these studies will attempt to achieve more consistent in vivo bone formation results which will be required for clinical translation. In addition the ability of the successful peptides to enhance the ability of suboptimal doses of BMP-2 to induce ectopic bone formation in this model may also be investigated.

Expected Results: It is expected that the peptides that are able to bind Smurf1 and enhance BMP-2 signaling will also induce bone in implants containing transduced MSCs in the rat model of ectopic bone formation. Further it is predicted that MSCs treated with lower doses of the same peptides will improve the bone induction by suboptimal doses of BMP-2. Both findings are interpreted as extremely promising strategies for inducing bone in a clinical setting and these strategies would be moved to the more challenging rabbit and non-human primate models.

Abbreviations: MSCs, mesenchymal stem cells; hMSC, human mesenchymal stem cells; P-Smad, phosphorylated Smad; R-Smad, receptor Smad: I-Smad, inhibitor Smad; PTD, protein transduction domain; siRNA, small interfering RNA; LMP, LIM mineralization protein; Smurf, Smad Ubiquitin Regulatory Factor; BMP-2, bone morphogenic protein-2; rhBMP-2, recombinant human bone morphogenic protein-2; Jab1, Jun Activation Domain Binding Protein; pfu, plaque forming units; MOI, multiplicity of infection.

As used herein, the when referring to treatment of cells, tissues or animals, the terms "BMP-2" and "rhBMP-2" are synonymous.

The present invention may be more fully understood by reference to the following non-limiting examples.

EXAMPLES

Example 1

LMP-1 Dramatically and Synergistically Increases the Responsiveness of Mesenchymal Stem Cells (MSCs) to BMP-2

It is known that LMP-1 induces bone but produces very small amounts of BMPs. In an effort to elucidate the mechanism behind this phenomena, the hypothesis that LMP-1 increases the responsiveness of cells allowing them to respond to lower levels of BMPs with respect to osteoblastice differentiation, was tested.

MSC cultures transfected with the chimeric Ad5F35 vector overexpressiong LMP-1 were treated with either LMP-1 (0, 1, 5, 10 pfu/cell) or BMP-2 (100 ng/mL) alone or in combination. Neither BMP-2 nor LMP-1 alone induce any bone nodule mineralization in human MSCs on day 21, but treating MSCs overexpressing LMP-1 (5-10 pfu/cell) with rhBMP-2 (100 ng/mL) induced dramatic bone nodule mineralization as shown by alizarin red staining. Thus, unexpectedly, concurrent exposure to LMP-1 enabled an ineffective dose of BMP-2 to facilitate bone formation suggesting that LMP-1 increases the BMP signaling pathway activity/sensitivity. The chimeric Ad5F35 vector, in which the Ad5 fiber protein is replaced with the Ad35 fiber protein, was used to reduce susceptibility to neutralizing antibodies also tranduces human MSCs more effectively than Ad5 vectors. (Yotnda P, Onishi H Heslop H E et al. *Gene Ther.* 2001;8:930-7; Gugala Z, Olmsted-Davis E A, Gannon F H, Lindsey R W, and Davis A R. *Gene Ther.* 2003;10:1289-96).

LMP-1 was also shown to increase the responsiveness of human MSCs to BMP-2 as evidenced by alkaline phosphatase mRNA levels and an increase in enzyme activity.

Example 2

LMP Variant (LMP-2) Does Not Induce Nodule Formation in Rat Calvarial Osteoblast Cultures Secondary rat calvarial osteoblasts do not spontaneously differentiate without exposure to a stimulus such as glucocorticoid (GC). Cells were transfected with plasmids containing three LMP (hLMP-1; hLMP-2 and hLMP-3) variants and assessed for multilayer mineralized nodule formation 14 days after treatment. Control cells received no treatment and all data were normalized to the control group. Overexpression of hLMP-1 resulted in nodule formation (225 nodules) comparable to that seen with GC (275 nodules). hLMP-3, which is a truncated version of LMP-1 also induced nodule formation (290 nodules). However, hLMP-2 which lacks a 45aa region failed to induce nodule formation (20 nodules), suggesting that the missing 45aa are required for LMP's osteoinductive properties.

Example 3

Detection of Smad1 and Phosphorylated Smad1 (P-Smad1)

Measuring activation of the BMP signaling pathway requires the ability to measure Smad1 and Smad5. SDS- PAGE separated cytoplasmic and nuclear protein blots were probed with Smad-1 specific antibody. A comparison of cytoplasmic and nuclear protein extracts from untreated pleuripotent cells demonstrated that most of the Smad1 (54 kDa) was detected in the cytoplasmic fraction.

For detection of P-Smad1 (phosphorylated Smad1) in the nucleus, SDS-PAGE blots of nuclear proteins were prepared from MSCs overexpressing LMP-1 at 4 and 8 hours following infection with Ad5F35-LMP-1. The blots were probed with primary antibody specific to P-Smad1. The binding of primary antibody was detected using the HRP-labeled second antibody after signal development by enhanced chemi-luminescence (ECL). A single band at the apparent size of 54 kDa showed an increase of phosphorylated Smad1 in the nuclear fraction as early as 4 hours in cells over-expressing LMP-1 compared to control MSCs not over-expressing LMP-1. Human MSCs treated with BMP-2 also have increased levels of cytoplasmic phosphorylated Smad1 in the presence of overexpressed LMP-1.

For detection of P-Smad1 (phosphorylated Smad1), in the cytoplasm, SDS-PAGE blots of cytoplasmic proteins were prepared from MSCs overexpressing LMP-1 at 4 and 8 hours following infection with LMP-1 delivered as Ad5F35-LMP-1. Cells were treated with rhBMP-2 at 100 ng/mL or 200 ng/mL alone or in combination with LMP-1 (5 pfu/cell). rhBMP-2 treatment at either 100 ng/mL or 200 ng/mL resulted in a small increase in cytoplasmic phosphorylated Smad1 (64 kDa band). Addition of rhBMP-2 (100 ng/mL)+ LMP-1 (5 pfu/cell) however, resulted in a significant increase (over 10 fold increase) in the amount of phosphorylated Smad1 protein which was not seen with LMP-1 at 5 pfu/cell alone. These data support the hypothesis that LMP-1 blocks the Smurf1-mediated degradation of unphosphorylated Smad1 resulting in a larger pool of Smad1 and therefore a greater amount of phosphorylated Smad1 is produced for a given amount of BMP-2.

Example 4

Investigation of Increased Smad1 Induced by BMP and LMP-1

To determine whether the increased level of Smad1 protein might be due to increased expression of Smad1, MSCs were treated with rhBMP-2 (100 ng/mL) or Ad5F35-LMP-1 (5 pfu/cell). Control cells were untreated. After 4 or 8 hrs total RNA was harvested and Smad1 mRNA was measured by real time RT-PCR. LMP-1 and BMP-2 each increased Smad1 mRNA by 4 hours, 5 fold and 6.2 fold, respectively. At 8 hours Smad1 mRNA was increased by 4.5 fold and 2 fold for LMP-1 and BMP-2 respectively. The data suggest that LMP-1 causes increased nuclear levels of P-Smad1 via increased expression of Smad1 mRNA, which results in increased Smad1 protein that can be phosphorylated by the BMP receptor kinase.

Given the short time frame of P-Smad1 accumulation in the nucleus shown above however, this mechanism is not the likely explanation for the short term (4 hr) increase. It is more likely a result of decreased degradation of P-Smads that is responsible for the short term regulatory mechanism.

Example 5

LMP-1 and BMP-2 Synergistically Increase Expression of Smad-regulated Genes

In order to measure immediate downstream markers of BMP signaling, mRNA levels of Dlx5, a gene known to be induced by the BMP-Smads was measured. MSCs were untreated or treated with BMP-2 (100 ng/mL), Ad5F35-LMP-1 (5 pfu/cell), or both. After 24 hr total RNA was harvested and Dlx5 mRNA levels measured by real time RT-PCR. Data are expressed as fold change in Dlx5 mRNA. Untreated cells exhibited 1 fold increase. Cells treated with BMP-2 demonstrated 6 fold increase, while cells treated with LMP-1 demonstrated 2 fold increase. A synergistic effect was seen on treatment with both LMP-1 (at 5 pfu/cell) and BMP-2 (at 100 ng/mL), showing 25 fold increase.

While protein levels were not measured in this study, methods are well known and include Western analysis and ELISA.

Example 6

Measurement of Other Smad-regulated Targets

Measurement of the mRNA and protein levels of Smad6, and BMP-2 can also be performed. For these studies, human MSCs are plated at $3 \times 10^4$ cells/well in 6-well plates, grown overnight, and treated with Ad5F35-LMP-1 (0, 5, 10 pfu/cell), BMP-2 (100 ng/ml) or both agents in combination or in series. The control treatment would be the vector, Ad5F35-GFP. After 1, 2, 4, 8, 12, 18, 24, 36, 48, and 72 hrs, cells are harvested for analysis of total RNA or cytoplasmic and nuclear protein. After reverse transcription, real-time PCR is performed using primers specific for human BMP-2 and Smad6. Similarly, secreted, cytoplasmic and nuclear proteins can be analyzed by ELISA using commercially available antibodies to the proteins of interest, with alkaline phosphatase conjugated secondary antibodies. Specificity of the antibody can be determined by Western blot to assure that there is only one immunoreactive species.

Intracellular BMP-2 is expected to show several immunoreactive bands corresponding to various cleavage steps during processing of pro-BMP-2. The processed BMP-2 protein will also likely be found largely in the medium, as it is rapidly secreted. Measurement of BMP-2 transcripts can be used for determining the relative effect of LMP-1 and BMP-2 on BMP-2 gene expression, as the majority of the protein measured in the medium from BMP-2 treated cells may be exogenously added as a treatment.

Example 7

LMP-1 is Associated with an 85 kDa Nuclear Protein

Recombinant LMP-1 was labeled with SBED-biotin transfer reagent and incubated as bait with nuclear proteins. Biotin transfer to target proteins was accomplished by photo-activation and decoupling was performed by reduction of bound protein-partners. Enrichment of biotinylated proteins was performed using neutravidin-beads. Biotinylated proteins were separated by SDS-PAGE and detected on Western blots using HRP-labeled neutravidin and ECL. The corresponding coomassie stained bands were excised for tryptic digestion and MALDI-TOF analysis. LMP-1 was seen to associate with three protein bands; one 85 kDa band and two smaller bands.

The smaller size bands were sequenced and represent cytoskeletal proteins likely involved with cellular localization of full length LMP-1 and not its osteoinductive properties. Based on partial sequence analysis, an 85 kDa band was investigated further (see below).

Example 8

Peptide Mass Profile Analysis of the 85 kDa Protein Binding to LMP-1

The SDS-PAGE separated LMP-1 binding protein bands were in-gel digested by 5% (w/w) trypsin. Molecular mass of tryptic-peptides was obtained by MALDI-TOF and analyzed by PepIdent. The resulting 85 kDa candidate protein matches from the data base were analyzed. Smurf1 and its splice-isoform variant showed the best ranking with peptide mass profile. Although the tryptic digestion was done on doublet protein bands, the unique identity was still able to be determined due to identical peptide profiles of both isoforms of Smurf1 in tryptic digestion. By comparison the peptide profile obtained did not match the peptide mass profile of Smurf2.

Example 9

The 85 kDa Protein Reacts with Smurf1/2 Antibody

Identity of the gel purified LMP-1 binding protein was verified by performing a Western blot using antibody that binds both Smurf1 and Smurf2. The doublet containing two protein bands, one running at 86 kDa and the other running at 84 kDa, were both immuno-reactive and probably represent two known splice variants of Smurf1 of similar molecular size rather than Smurf1 and Smurf2. Based on molecular size, immuno-reactivity with Smurf1/2 antibody in Western blots, and tryptic-peptide profiles, the putative LMP-binding protein was identified as Smurf1.

Example 10

Immunoprecipitation Endogenous Smurf1 and LMP-1 in MSCs

Human MSCs were plated at $3 \times 10^4$ cells/well in 6-well plates, grown overnight, and treated with Ad5F35-LMP-1 (0, 5, 10 pfu/cell), or Ad5F35-GFP. After 2, 4, 8, 12, 24, and 48 hrs, cells were harvested and nuclear proteins mixed with LMP-1 or Smurf1 antibody and subjected to immunoprecipitation. Eluted proteins were separated by SDS-PAGE and Western analysis performed using LMP-1 or Smurf1 antibodies.

Nuclear protein extracts of untreated MSCs were incubated with LMP-1 antibody and immunoprecipitated using protein-A beads. The immunoprecipitated proteins were concentrated and analysed in Western blots with LMP-1 and Smurf1/2 antibody, separately. Both endogenous LMP-1 and Smurf1 were present in the complex immunoprecipitated with the LMP-1 antibody from untreated MSCs. This observation was confirmed by detection of LMP-1 when Smurf1 antibody was used for the immunoprecipitation.

Other studies demonstrated interaction of these proteins in the nuclear fraction. It is unknown whether the Smurf1/LMP-1 interaction will also be observed in the cytoplasm but these studies can be performed according to the methods described herein.

Example 11

LMP-1 Interacts with Smurf1 Via the Smurf1 WW Domain

Blots of SDS-PAGE resolved nuclear proteins from MSCs showed a predominant band at 85 kDa when probed with Smurf1 WW-domain antibody in Western blots. Pre-incubation of LMP-1 (10 uM) with these blots inhibited Smurf1 antibody binding. Binding competition between LMP-1 protein and WW-antibody towards the same target sequence suggests that the interaction with LMP-1 occurs at the WW-domain(s) of Smurf1. The WW-domains are the region that enables Smurf1 to bind to critical BMP signaling Smad1 and Smad5 and target them for degradation. These data support the hypothesis that LMP-1 blocks Smurf1 from interacting with and targeting Smad1 and Smad5.

Not only did LMP-1 inhibit binding, truncated LMP variants also inhibit Smurf WW-domain antibody binding to Smurf1. Blots of SDS-PAGE resolved nuclear proteins from untreated MSCs were incubated with the antibody specific for the Smurf1 WW-domain. Both full length recombinant LMP-1 and recombinant LMP-1t (a C-terminal truncated version of LMP-1), when preincubated on the blots, were able to prevent the WW-domain antibody from binding to Smurf1. These data suggest that the LIM domains (located at the C-terminus of LMP-1) are not needed for the direct interaction with Smurf1.

Example 12

Characterization of the Binding Properties of Smurf1, LMP-1, Smad1, and Smad5 Using Purified Proteins to Confirm Competitive Binding of LMP-1

Recombinant Smad1 and Smad5 are prepared by bacterial expression and purification. Smads and LMP-1 are then fluorescently labeled. The Enzyme Linked Sorbent Assay (ELSA) described herein is performed in microtiter plates. Binding curves for evaluating the competitive binding to Smurf1 of fluorescently labeled LMP-1 with unlabeled Smad1 or Smad5 are then obtained. Conversely, the competitive binding of fluorescently labeled Smads with unlabeled LMP-1 may also be measured. Fluorescence is monitored using a Biolumin 960 combined fluorescence and absorbance microplate reader. Scatchard analyses, well known in the art, can serve to assess the binding affinity, dissociation constants, number of binding sites, and stoichiometry for each protein involved in the interaction.

The results can then predict competition between LMP-1 and Smads for binding Smurf1 at one or two sites. Competitive binding at two sites might occur, as Smurf1 contains two WW domains and it is uncertain whether all or some of the proteins bind one or both sites. If Smad5 does not accumulate in the nucleus it might not be expected to compete with LMP-1 for

Example 13

Identification of Two Regions within LMP-1 with High Affinity for Smurf1 WW-Domains On finding that full length LMP-1 binds Smurf1 WW domains, comparative sequence analysis of three LMP-1 variants was performed and identified a 45 amino acid "osteoinductive region" that is present in the two LMP-1 isoforms that induce bone formation, but is not present in a third isoform that fails to induce bone. These LMP variants (LMP-1, LMP1t and LMP-3) were created which contain a unique peptide sequence, (AADPPRYTFAPSVSLNKTARPFGAPPPADSAPQQNG; SEQ ID NO: 33) within a larger osteoinductive region which includes two Smurf1 WW-domain interaction sites (WW interacting site A comprising the sequence ADPPRYTFAP; herein referred to as SEQ ID NO: 34; and WW interacting site B comprising the sequence GAPPPADSAP; herein referred to as SEQ ID NO: 35). The WW domain interacting sites are absent in a non-osteogenic LMP variant (LMP-2). The 45 amino acid osteoinductive region appears to be critical for the bone-forming activing of LMP. Two LMP variants (LMP 1t and LMP-3) are truncated at the carboxy-terminus, and do not contain the LIM domains, but do induce bone formation. Thus, it is the 45 amino acid osteoinductive region and not the LIM domains that are required for bone formation (Liu, Y, et. al.; *J. Bone Min. Res.,* 2002:17:406-414).

Slot blots prepared with recombinant Smurf1 and hybridized with biotin-labeled LMP variants demonstrated that only the LMP variants containing the WW-domain interaction sites (LMP-1, LMP-1t and LMP-3) were able to bind to Smurf1.

To determine which of the two WW-domain interaction sites were required for the binding of LMP with Smurf1, two mutant LMP-1 proteins that are mutated in either WW interaction site A (Prolines at positions 100 and 101 of the 457 amino acid parent protein being converted to Alanine, herein incorporated as SEQ ID NO: 36; LMP-1Δ WWA) or site B (Prolines at positions 122, 123 and 124 of the 457 amino acid parent protein being converted to Alanine, herein incorporated as SEQ ID NO: 37; LMP-1Δ WWB) were prepared. The mutations remove proline residues that are required for interaction with the Smurf1 WW domain and disrupt the PY motif in each of the two sites.

```
LMP-1ΔWWA-SEQ ID NO: 36;
<200> SEQUENCE CHARACTERISTICS:
<210> SEQ ID NO 36
<211> LENGTH: 457
<212> TYPE: PRT
<213> ORGANISM: Homo sapiens
<400> SEQUENCE: 36
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
                 20                  25                  30

Leu Thr Pro Gly Gly Lys Ala Ala Gln Ala Gly Val Ala Val Gly Asp
             35                  40                  45

Trp Val Leu Ser Ile Asp Gly Glu Asn Ala Gly Ser Leu Thr His Ile
         50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Ala Ala Arg Tyr Thr Phe Ala Pro Ser Val Ser Leu
                100                 105                 110

Asn Lys Thr Ala Arg Pro Phe Gly Ala Pro Pro Ala Asp Ser Ala
             115                 120                 125

Pro Gln Gln Asn Gly Gln Pro Leu Arg Pro Leu Val Pro Asp Ala Ser
         130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
         195                 200                 205

Pro Trp Pro Gly Pro Thr Ala Pro Ser Pro Thr Ser Arg Pro Pro Trp
     210                 215                 220
```

-continued

```
Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
            245                 250                 255

Ser Arg Thr Ser Ile Val Gln Ala Ala Gly Gly Val Pro Gly Gly
        260                 265                 270

Gly Ser Asn Asn Gly Lys Thr Pro Val Cys His Gln Cys His Lys Val
    275                 280                 285

Tyr Arg Gly Arg Tyr Leu Val Ala Leu Gly His Ala Tyr His Pro Glu
290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Ile Thr Gly Glu Ile
                340                 345                 350

Met His Ala Leu Lys Met Thr Trp His Val His Cys Phe Thr Cys Ala
            355                 360                 365

Ala Cys Lys Thr Pro Ile Arg Asn Arg Ala Phe Tyr Met Glu Glu Gly
        370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
                420                 425                 430

Ile Asn Leu Glu Gly Lys Thr Phe Tyr Ser Lys Lys Asp Arg Pro Leu
                435                 440                 445

Cys Lys Ser His Ala Phe Ser His Val
    450                 455

LMP-1ΔWWB- SEQ ID NO: 37
<200> SEQUENCE CHARACTERISTICS:
<210> SEQ ID NO 37
<211> LENGTH: 457
<212> TYPE: PRT
<213> ORGANISM: Homo sapiens
<400> SEQUENCE: 37
Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
                20                  25                  30

Leu Thr Pro Gly Gly Lys Ala Ala Gln Ala Gly Val Ala Val Gly Asp
            35                  40                  45

Trp Val Leu Ser Ile Asp Gly Glu Asn Ala Gly Ser Leu Thr His Ile
        50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Ala Ala Ala Asp Ser Ala
        115                 120                 125
```

-continued

```
Pro Gln Gln Asn Gly Gln Pro Leu Arg Pro Leu Val Pro Asp Ala Ser
    130             135                 140
Lys Gln Arg Leu Met Glu Asn Thr Glu Asp Trp Arg Pro Arg Pro Gly
145             150                 155                 160
Thr Gly Gln Ser Arg Ser Phe Arg Ile Leu Ala His Leu Thr Gly Thr
                165                 170                 175
Glu Phe Met Gln Asp Pro Asp Glu Glu His Leu Lys Lys Ser Ser Gln
            180                 185                 190
Val Pro Arg Thr Glu Ala Pro Ala Pro Ala Ser Ser Thr Pro Gln Glu
        195             200                 205
Pro Trp Pro Gly Pro Thr Ala Pro Ser Pro Thr Ser Arg Pro Pro Trp
    210             215                 220
Ala Val Asp Pro Ala Phe Ala Glu Arg Tyr Ala Pro Asp Lys Thr Ser
225             230                 235                 240
Thr Val Leu Thr Arg His Ser Gln Pro Ala Thr Pro Thr Pro Leu Gln
                245                 250                 255
Ser Arg Thr Ser Ile Val Gln Ala Ala Ala Gly Gly Val Pro Gly Gly
            260                 265                 270
Gly Ser Asn Asn Gly Lys Thr Pro Val Cys His Gln Cys His Lys Val
            275                 280                 285
Ile Arg Gly Arg Tyr Leu Val Ala Leu Gly His Ala Tyr His Pro Glu
    290                 295                 300
Glu Phe Val Cys Ser Gln Cys Gly Lys Val Leu Glu Glu Gly Gly Phe
305                 310                 315                 320
Phe Glu Glu Lys Gly Ala Ile Phe Cys Pro Pro Cys Tyr Asp Val Arg
                325                 330                 335
Tyr Ala Pro Ser Cys Ala Lys Cys Lys Lys Lys Ile Thr Gly Glu Ile
            340                 345                 350
Met His Ala Leu Lys Met Thr Trp His Val His Cys Phe Thr Cys Ala
        355                 360                 365
Ala Cys Lys Thr Pro Ile Arg Asn Arg Ala Phe Tyr Met Glu Glu Gly
    370                 375                 380
Val Pro Tyr Cys Glu Arg Asp Tyr Glu Lys Met Phe Gly Thr Lys Cys
385                 390                 395                 400
His Gly Cys Asp Phe Lys Ile Asp Ala Gly Asp Arg Phe Leu Glu Ala
                405                 410                 415
Leu Gly Phe Ser Trp His Asp Thr Cys Phe Val Cys Ala Ile Cys Gln
            420                 425                 430
Ile Asn Leu Glu Gly Lys Thr Phe Tyr Ser Lys Lys Asp Arg Pro Leu
        435                 440                 445
Cys Lys Ser His Ala Phe Ser His Val
    450                 455
```

Recombinant Smurf1 was run on SDS-PAGE, transferred to membrane, and incubated with buffer, LMP-1 protein, LMP-2 protein (negative control, no osteoinductive region), LMP-1ΔWWA or LMP-1ΔWWB. After washing, Smurf1 WW domain antibody was applied and then detected with HRP-labeled secondary antibody. Slot blots of competitive binding assays were analyzed as before and it was found that only WW-domain interaction site B was required for the interaction with Smurf1. The specificity of these interaction sites was confirmed by demonstrating that LMP-1 was no longer able to bind to a mutant form of Smurf1 which had its WW2 domain deleted (Smurf1ΔWW2).

Example 14

Peptide Mimics of LMP-1

To design and test molecules that mimic the LMP-1 interaction with Smurf1, known crystallography data and homology modeling of related homologues similar to the WW-2 domain in Smurf1 and the two potential interacting motifs in LMP-1 (WW-A and WW-B) as defined by iSPOT were used (Brannetti, B. and Helmer-Citterich, M., *Nucleic Acids Res.* 2003; 31:3709-3711). The MODELLER program was used to assign structure to the two interacting elements and to model templates. The designed Smurf1 WW-2 template showed a close (up to 70%) match to the coordinates of crystallographic data available for homologous WW domains from the protein data bank (PDB) (Fiser, A. and Sali, A., *Med. Res. Rev.* 2003; 374:461-491). DOCKING and SSA (Surface Solvent Accessability) programs were then used to define the key residues in each binding partner (Morris, G. M., Goodsell, D. S., Huey, R., and Olson, A. J., *J. Comput. Aided Mol.Des.*, 1996, 10:293-304). A directory of commercially available low molecular weight and cell penetrable chemicals were screened using the LUDI program with both complimentary screening (WW-2) and analogue screening (WW-A or WW-B) to identify candidate compounds (Honma, T., *Med. Res. Rev.* 2003, 23:606-632).We used computational mutagenesis to eliminate non-specific compounds and cross-matched the complimentary and analogue compound lists to arrive at 75 candidate compounds for each WW interacting domain of LMP-1. The specificity of the LMP motif that interacts with Smurf1 was confirmed and it was determined that the activity of the full length LMP protein could be replicated by a small peptide. We synthesized small peptides comprising various portions of the osteoinductive region, (KPQKASAPAADPPRYTFAPSVSLNKTARPFGAPPPADSAPQQNGQPLRPLVPDASKQRLM; herein referred to as SEQ ID NO: 38, BOLDED fragments represent the WW-domain interacting sites, with ADPPRYTFAP representing Site A, SEQ ID NO: 34 and GAPPPADSAP representing Site B, SEQ ID NO: 35) containing one, two, or none of the putative LMP WW-domain interacting sites. The Table below lists the ces of Peptide 1, 3, 5, and 7 that were designed to the osteogenic region of LMP-1. These peptides were chemically synthesized, HPLC purified for in vivo bone formation studies. Only peptide 7 is acetylated at N-terminus, and was therefore not expected to alter the peptide function.

TABLE 5

Peptide mimics

| Peptide # | SEQ ID NO: | Amino Acid Sequence |
|---|---|---|
| 1 | 39 | H₂N-APSVSLNKTARPFGAPPPADSAGGRRQRRTSKLMKR-CONH₂ |
| 3 | 40 | H₂N-KPQKASAPAADPPRYTFAPSVSGGRRQRRTSKLMKR-CONH₂ |
| 5 | 41 | H₂N-ASAPAADPPRYTFAPSVSLNKTARPFGAPPPADSAPQQNGGGRRQRRTSKLMKR-CONH₂ |
| 7 | 42 | Acetyl-GAPPPADSAPQQNGQPLRPLVPDASKQRLMGGRRQRRTSKLMKR-NH₂ |

Competition studies (across the range of 0.001 uM to 1.0 uM, and including 0.001, 0.01, 0.1 and 1 uM) of the peptides revealed that the two peptides that contained intact WW-domain interacting Site B were able to compete with full length LMP-1 in a dose dependent manner as well as with Smad1 and Smad5 for binding with Smurf1 at concentrations of 1.0 uM and 10 uM.

This result is consistent with the mutational analysis above establishing Site B as the more critical site in LMP. To determine if the ability of the small LMP-derived peptides to competitively bind Smurf1 has physiologic significance, the peptides were linked to a protein transduction domain (PTD) that facilitates entry into cells (Sequence: RRQRRTSKLMKR, herein incorporated as SEQ ID NO: 32). We found that only peptide 7 had the ability to induce bone formation in a rat ectopic bone formation assay.

Example 15

Osteoinductive Region Fusion Peptides

To verify that the 36 amino acid sequence (AADPPRYTFAPSVSLNKTARPFGAPPPADSAPQQNG; SEQ ID NO: 33) is responsible for the LMP-1 interaction with Smurf1, an "osteoinductive region-fusion peptide" (PTD-LMP-1/OR) containing a PTD that readily enters cells (RRQRRTSKLMKR, herein incorporated as SEQ ID NO: 32) was designed. Initial studies were performed to determine a dose of PTD-LMP-1/OR that enhanced the effect of 100 ng/ml BMP-2 to mineralize hMSCs. Once two effective doses, 15 nM and 17.5 nM, were established, hMSCs were plated at $3\times10^4$ cells/well in 6-well plates, grown overnight, and treated with PTD-LMP-1/OR, BMP-1 (100 ng/ml) or both agents. The control was PTD-βGal. After 1, 2, 4, 8, 12, 24, 36, 48, and 72 hrs, cells were harvested and total RNA plus cytoplasmic and nuclear protein fractions prepared. The nuclear protein fraction from the untreated sample was analyzed for the ability of purified PTD-LMP-1/OR to compete with Smurf1 antibody binding to Smurf1 on a Western blot. All protein samples were analyzed for the presence of P-Smad1 and P-Smad5 by Western blot using appropriate antibody. All RNA samples were analyzed by real-time RT-PCR for mRNA levels of Dlx5, Smad6, and BMP-2. Similarly, protein fractions were analyzed by ELISA using commercially available antibodies to Dlx5, Smad6, and BMP-2.

The results illustrate that the 36aa peptide has all the ability of full length LMP-1 to compete with WW domain antibody binding, to induce increased nuclear levels of P-Smad1 and P-Smad5, and to increase expression of BMP/Smad regulated genes. It is noted that PTD-fusion peptide derivatives of one of the osteoinductive LMP isoforms (LMP-3) have been shown by others to induce bone formation (Pola E, Gao W, Zhou Y et al. *Gene Ther.* 2004; 11:683-93).

Example 16

Full Length and Truncated LMP-1 Variants Form Bone in Ectopic and Orthotopic Models in vivo Bone marrow cells and leukocytes were transfected with the cDNA of full length or truncated LMP-1 lacking LIM domains. Collagen discs containing the engineered cells were implanted subcutaneously into athymic rats. Histology of the implants showed ectopic and orthotopic bone formation. New bone trabeculae lined with osteoblasts were seen in the implants containing cells overexpressing truncated LMP-1 (LMP-1t) and the absence of new bone in implants containing control cells. This demonstrates that genetically engineered cells can form bone in vivo and confirms that the LIM domains of LMP-1 are not needed for bone formation.

Example 17

Bone Marrow Cells Transfected with LMP-1 Induce Bone in the Rat Model of Spine Fusion Spine fusion is a more challenging bone formation model than an ectopic site. Rats were implanted with carrier soaked with bone marrow cells which had been transfected with the cDNA of LMP-1 in an active or inactive form. Lateral radiography of the animals at 4 weeks indicated solid spine fusion when the marrow cells expressed active LMP-1 protein but no evidence of bone formation was seen when the marrow cells had been transfected with an inactive form of LMP-1. These data indicate that genetically engineered bone marrow cells can induce rat spine fusion.

Example 18

A TAT-LMP-1 Fusion Protein Enters the Nucleus of Cells and Forms Bone in vivo Fusion proteins that contain an 11aa sequence, found in the HIV protein Tat, are known to readily enter cells within minutes (Nagahara H, Vocero-Akbani A M, Snyder E L et al. *Nat.Med.*1998; 4:1449-52). This method of protein delivery is superior to adenoviral gene transfer because it avoids immune response issues. To confirm that a LMP fusion protein would enter cells, a FITC labeled LMP-1 Tat fusion protein (TAT-LMP-1) was synthesized and fluorescence monitored for localization in the MSCs when treated at doses of 10, 25 and 100 nM. The fusion protein readily entered nucleated blood cells in a dose dependent manner with 2, 25 and 90% of the cells positive for the label, respectively. Western blots from another experiment confirmed the ability of TAT-LMP-1 to enter the nucleus. X-rays showed good bone formed on collagen discs in rats implanted with cells treated for 30 min with TAT-LMP-1. The bone induction with TAT-LMP-1 was not always consistent between experiments and thus this was not an optimal "stand alone" strategy for bone formation. A better understanding of the mechanism of action of LMP-1 and a designer small molecule may allow it to perform more consistently as a "stand alone" initiator of bone formation or as a means of increasing the responsiveness to BMPs.

Example 19

LMP-1 siRNA

In an effort to selectively inhibit expression of specific genes in order to elucidate aspects of the proposed LMP-1 mechanism of action, siRNA were designed to target LMP-1. Use of small inhibitory RNAs (siRNAs) to destroy specific mRNAs has become the method of choice for specifically silencing expression of genes (Martinez J, Patkaniowska A, Urlaub H, Luhrmann R, and Tuschl T. *Cell* 2002; 110:563-74; Maeda S, Hayashi M, Komiya S, Imamura T, and Miyazono K. *EMBO J.* 2004; 23:1-12).

Conditions for siRNA treatment were first optimized and MC3T3-E1 cells were transfected with siRNA (10 pmol) to LMP-1 disclosed herein and according the methods disclosed herein. LMP-1 mRNA levels were reduced by 90% 48 hrs after siRNA treatment as compared to no treatment. Reduced bone nodule mineralization was also observed in addition to the decrease in LMP-1 mRNA levels.

Example 20

Smurf1 siRNA

In an effort to demonstrate the effects of reducing the level of functional Smurf1 to support the hypothesis that LMP-1 acts by decreasing the amount of Smurf1 available to bind to Smad1/5, siRNA to Smurf were designed and tested for target reduction in TE85 human osteosarcoma cells. Cells were treated according the methods taught herein and total RNA was harvested and Smurf1 mRNA levels measured by RT-PCR using primers specific for Smurf1. Smurf2 mRNA levels were also measured using specific primers and these levels did not change. There was a single product of each primer set which was sequenced to confirm its identity. The results indicate that Smurf1 siRNA produced a dose-dependent decrease in Smurf1 mRNA levels.

Example 21

Osterix Message in Human MSCs

Osterix is a novel zinc finger-containing transcription factor required for osteoblast differentiation and bone formation. Human MSCs were treated with Ad5/35LMP-1 (0, 1, 5, 10 pfu/cell) with and without BMP-2 (100 ng/mL) and harvested for RNA at day 8. RNA was isolated and osterix mRNA quantified by RT-PCR with the osterix primers. Data was normalized to 18S. These data illustrate that LMP-1 increased the responsiveness of human MSCs to BMP-2 as evidenced by increase in osterix message. The data are summarized in Table 6.

TABLE 6

Increase in Osterix mRNA

| Treatment | No treatment | BMP-2 | LMP-1 (5 pfu/cell) | LMP-1 (10 pfu/cell) | LMP-1 (5 pfu/cell) + BMP-2 | LMP-1 (10 pfu/cell) + BMP-2 |
|---|---|---|---|---|---|---|
| Fold Increase in Osterix mRNA | 1.0 | 88.3 | 0.4 | 0.4 | 178.6 | 424.6 |

Example 22

Overexpression of LMP-1 Increases BMPRIA (ALK3) Levels in Human MSCs

Human MSCs were treated for 8 hours with rhBMP-2 (100 ng/mL) alone or with Ad5F35-LMP-1 (5 pfu/cell) and cytoplasmic proteins were enriched for the plasma membrane fraction and resolved by SDS-PAGE separation. The blot was then probed with antibody specific for the Type IA BMP receptor (BMPR1A/ALK3) and a predominant band at the expected size for BMPR1A (55 kDa) was observed. rhBMP-2 treatment (100 ng/mL) resulted in an expected increase in BMPR1A over untreated control cells. However, when rhBMP-2 was given in the presence of LMP-1 a significantly greater increase in the BMPR1A levels was observed. These data support the hypothesis that LMP-1 interrupts the Smurf1/Smad6 mediated degradation of BMP receptors.

Example 23

LMP-1 Interacts with Jun Activation Domain Binding Protein (Jab1)

The yeast-two-hybrid (Y2H) system (Clontech) was used to identify other proteins which could interact with LMP-1. Positive clones were selected based on Y2H screening of a bone marrow library. The sequencing and database matching of 10 putative positive clones identified Jab1 as a likely candidate binding partner for LMP-1. It was then determined if this association occurred in cells. Immunoprecipitation of cytoplasmic proteins using LMP-1 antibody beads demonstrated that Jab1 was found in complexes with LMP-1.

Although these data demonstrate that an association between Jab1 and LMP-1 occurs in cells, they do not establish direct binding of the two proteins.

Example 24

LMP-1 Binds to Jab1

To demonstrate that LMP-1 binds Jab1 directly, cytoplasmic proteins from human osteoblastic TE-85 cells were separated by SDS-PAGE and blots were probed with Biotin-LMP-1. The bound biotin-LMP-1 was detected using neutravadin-HRP. Two bands were present on the blot and demonstrated that LMP-1 is capable of binding directly to both Smurf1 (85 kDa) and Jab1 (38 kDa). The identity of these two bands were confirmed by staining with antibody specific to Smurf1 and Jab1. These blots provide evidence that LMP-1 interacts directly with Jab1 supporting the hypothesis that LMP-1 may interrupt the binding of Jab1 to one of its targets (Smad4).

Example 25

Identification of Binding Interactions with Jab1

While not identified herein, the sites or protein domains necessary for interaction between LMP-1 and Jab1 can be determined in the same manner as those for the interaction between LMP-1 and Smurf1 (see Examples 13 and 14). Once identified, peptides containing those sites or domains may be designed modulate the interaction of the proteins.

Example 26

LMP-1 Overexpression Increases Nuclear Smad4 Levels in Human MSCs

To demosntreate the effects of LMP-1 overexpression and rhBMP-2 treatment on Smad4, human MSC's were treated with rhBMP-2 (100 ng/mL), or LMP-1 (Ad5F35, MOI=5) for 8 hours. SDS-PAGE separated nuclear protein blots were probed with Smad4 specific antibody. A 66 kDa band representing nuclear Smad4 was seen to increase 8 hours after LMP-1 treatment. A nonspecific band (running above the 66 kDa band) was also seen. These data support the hypothesis that LMP-1, presumably via its interaction with Jab1, decreases the targeting of Smad4 for proteasomal degradation thereby resulting in increased Smad4 levels. As was expected, rhBMP-2 alone did not affect the nuclear Smad4 levels as it does not interact with Jab1. Collectively these data support the direct interaction of LMP-1 and Jab1 in cells and the fact that LMP-1 can increase the levels of Smad4 in cells. This may represent a third regulatory point for LMP-1 to modulate cellular responsiveness to BMPs since Smad4 is required for nuclear transport of activated R-Smads.

Example 27

Screening of LMP-1 Mimics

To identify small molecules that mimic the effect of LMP-1 on induction of bone formation, and have properties that make it more clinically convenient, multiple compounds may be screened which contain or mimic the more important LMP-1 interacting domain (B). These compounds are tested for their ability to compete with LMP-1 for Smurf1 binding.

In these studies, recombinant Smurf1 is applied to wells of a 96 well plate. After removing excess Smurf1, test compounds (in excess) are pre-incubated with Smurf1 followed by incubation of the Smurf1 complexes with recombinant biotin-LMP-1. Biotin-LMP-1/Smurf1 is detected using Strepavidin-alkaline phosphatase. Absorbance is determined at 405 nm using the SpectraMax M2 microtiter plate reader. Compounds that block Biotin-LMP-1 binding may then be re-screened using appropriate lower amounts of the compound to determine the $IC_{50}$ (dose that prevents 50% of the maximum LMP-1 binding). Those compounds with the lowest $IC_{50}$ are considered the most efficacious and can then be screened for cellular effects. The $IC_{50}$ is used to determine the dose of each compound that we will screen.

Example 28

Screening Compounds in vitro

Candidate compounds that most efficiently inhibit binding of LMP-1 to Smurf1 in binding competition assays are further evaluated for their ability to mimic LMP-1 in cells. One appropriate cell line are mesenchymal stem cells (MSCs) and appropriate endpoints include an increase BMPR1A levels and an increase in luciferase production from a Smad-activated reporter construct.

In these studies, human MSCs are plated at $3\times10^4$ cells/well in 6-well plates, grown overnight, and treated with candidate compounds at the $IC_{50}$ dose and two doses above and below that dose. Ad5F35LMP-1 and Ad5F35GFP are applied as positive and negative controls. After 1, 2, 4, 8, 12, 24 and 48 hrs, cells are harvested and plasma membrane enriched fractions prepared. Fractions are subjected to SDS-PAGE and Western analysis using BMPR1A specific antibody. In the second set of experiments MSCs plated as above and transfected with a 9×GCCG/Smad-activated luciferase reporter construct (SEQ ID NO: 43) are incubated with all compounds (at the successful dose) that increased BMPR1A in the first experiment. These studies are performed in the presence or absence of 100 ng/mL BMP-2.

The results will allow for identification of compounds and doses of compounds that will mimic the effect of LMP-1 on the particular endpoint. It is also expected that doses of candidate compounds that successfully increase BMPR1A will increase luciferase activity somewhat when applied alone, but will greatly enhance the effect of BMP-2 on the luciferase activity.

Example 29

Screening Compounds in vivo

Compounds found to activate the BMP/Smad signaling pathway in vitro can then be screened in vivo for effects on induction of bone in the rat model of ectopic bone formation described herein.

Example 30

Synergy Screening

Once compounds that induce bone formation have been identified, those compounds are then tested in combination with low doses of BMP-2 to determine whether there are synergistic effects (as demonstrated in other examples herein) that might lower the required dose of either agent.

To evaluate potential synergy, we have identified herein a dose of BMP-2 (2.5 ug) that induces bone formation in only 50% of the implants and a lower dose (1 ug) that fails to induce bone formation in the rat model.

In the synergy studies, multiple doses of each of several candidate compounds are tested in cell culture studies of enhancement of BMP-2 signaling in MSCs. These studies test the ability of each compound to enhance the efficacy of a suboptimal dose of BMP-2 (2.5 ug) to make bone in more than 50% of the implants. The positive control is MSCs treated with TAT-LMP-1 (0.625 nM); negative controls include MSCs alone and BMP-2 (2.5 ug) alone. MSCs (1-2M) are mixed with appropriate doses of compounds in a 100 uL total volume and placed on a collagen disc. The disc is implanted subcutaneously on the chest of athymic rats and explanted after 4 weeks. Bone formation is evaluated by palpation, x-ray and semi-quantitative scoring of non-decalcified histologic sections (Edwards, J. T., Diegmann, M. H., and Scarborough, N. L., *Clin. Orthop.*, 1998, 219-228). The most promising compounds are tested twice more to determine the best one or two compounds to be used in future experiments in higher animals.

If the LMP-1 enhancement of BMP-2 efficacy to induce bone cannot be emulated by the chemical compounds that are screened, the need to also mimic the LMP-1/Jab1 interaction can be examined as the control of Smurf4 levels could be a rate-limiting step.

SEQUENCE LISTING

```
<160> NUMBER OF SEQ ID NOS: 43

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttctgagctt cgatgtgtgt ga                                              22

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catcatggat tccttcaagg tagtg                                           25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
catcgatgct cagcacccag tcacc                                           25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accctgtctg aggagcgtgt a                                               21

<210> SEQ ID NO 5
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 5
accaaagcgt ccacagcttt                                                   20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caccaagatg tgtaccattc gaa                                               23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaagagccca tctgagtaag ga                                                22

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggatctgtcc gattctacat tgtct                                             25

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtccggtgc tcccagtac                                                    19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggagttggcc gcctctctag                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 11
tggcgagtta cacgccatag                                              20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgccgagcga gatcaaagg                                               19

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtagcgcggc caaaagc                                                 17

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tccaagagac atgttaggat aagca                                        25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tccacgtaca aagggtgtct cttac                                        25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cccagagacc ttaacagtgt gaact                                        25

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 17
ttgagttggc actggtgatt ca                                              22

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctcggttgt gttcgtcttc ttt                                             23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcctattcgg tctctggact gaa                                             23

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcagacgccc cgacctt                                                    17

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
attggcaagc agtggtctag aga                                             23

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA sequence
<220> FEATURE:
<223> OTHER INFORMATION: Description of Artificial Sequence: Synthetic
      siRNA sequence

<400> SEQUENCE: 22
ccuugcaaag aaagacuuct t                                               21

<210> SEQ ID NO 23
<211> LENGTH: 21
<212> TYPE: DNA
<213> ORGANISM: Artificial Sequence
<220> FEATURE:
```

-continued

<223> OTHER INFORMATION: Description of Combined DNA/RNA Molecule:
      Synthetic siRNA sequence
<220> FEATURE:
<223> OTHER INFORMATION: Description of Artificial Sequence: Synthetic
      siRNA sequence

<400> SEQUENCE: 23
gguggugguu gauggaucut t                                            21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA sequence
<220> FEATURE:
<223> OTHER INFORMATION: Description of Artificial Sequence: Synthetic
      siRNA sequence

<400> SEQUENCE: 24
gcucagagua ucgaugaaat t                                            21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic siRNA sequence
<220> FEATURE:
<223> OTHER INFORMATION: Description of Artificial Sequence: Synthetic
      siRNA sequence

<400> SEQUENCE: 25
agaccuucua cuccaagaat t                                            21

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgcccccgcc gcggacgcag cacggtacac ctttgcac                          38

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtgcaaaggt gtaccgtgct gcgtccgcgg cggggcg                           38

<210> SEQ ID NO 28
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
ggcccggccc tttggggcgg cagcagcagc tgacagcgcc ccgcaac          47
```

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
gttgcggggc gctgtcagct gctgctgccg ccccaaaggg ccgggcc          47
```

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
gtgtgaactg tgatgaactt aatcaccagt gccaactc                    38
```

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
gagttggcac tggtgattaa gttcatcaca gttcacac                    38
```

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Gln Arg Arg Thr Ser Lys Leu Met Lys Arg
 1               5                   10

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ala Asp Pro Pro Arg Tyr Thr Phe Ala Pro Ser Val Ser Leu Asn
 1               5                   10                  15

Lys Thr Ala Arg Pro Phe Gly Ala Pro Pro Ala Asp Ser Ala Pro
             20                  25                  30

Gln Gln Asn Gly
         35

<210> SEQ ID NO 34
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 34

Ala Asp Pro Pro Arg Tyr Thr Phe Ala Pro
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ala Pro Pro Pro Ala Asp Ser Ala Pro
 1               5                  10

<210> SEQ ID NO 36
<211> LENGTH: 457
<212> TYPE: PRT
<213> ORGANISM: Homo sapiens

<400> SEQUENCE: 36

Met Asp Ser Phe Lys Val Val Leu Glu Gly Pro Ala Pro Trp Gly Phe
 1               5                   10                  15

Arg Leu Gln Gly Gly Lys Asp Phe Asn Val Pro Leu Ser Ile Ser Arg
                20                  25                  30

Leu Thr Pro Gly Gly Lys Ala Ala Gln Ala Gly Val Ala Val Gly Asp
            35                  40                  45

Trp Val Leu Ser Ile Asp Gly Glu Asn Ala Gly Ser Leu Thr His Ile
        50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                85                  90                  95

Pro Ala Ala Asp Ala Ala Arg Tyr Thr Phe Ala Pro Ser Val Ser Leu
            100                 105                 110

Asn Lys Thr Ala Arg Pro Phe Gly Ala Pro Pro Pro Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro Trp
    210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255
```

```
Ser Arg Thr Ser Ile Val Gln Ala Ala Gly Gly Val Pro Gly Gly
        260                 265                 270

Gly Ser Asn Asn Gly Lys Thr Pro Val Cys His Gln Cys His Lys Val
    275                 280                 285

Ile Arg Gly Arg Tyr Leu Val Ala Leu Gly His Ala Tyr His Pro Glu
        290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Ile Thr Gly Glu Ile
            340                 345                 350

Met His Ala Leu Lys Met Thr Trp His Val His Cys Phe Thr Cys Ala
                355                 360                 365

Ala Cys Lys Thr Pro Ile Arg Asn Arg Ala Phe Tyr Met Glu Glu Gly
        370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Arg Pro Leu
        435                 440                 445

Cys Lys Ser His Ala Phe Ser His Val
    450                 455

<210> SEQ ID NO 37
<211> LENGTH: 457
<212> TYPE: PRT
<213> ORGANISM: Homo sapiens

<400> SEQUENCE: 37

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Ala Ala Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
```

```
                    165                 170                 175
Glu Phe Met Gln Asp Pro Asp Glu Glu His Leu Lys Lys Ser Ser Gln
                180                 185                 190

Val Pro Arg Thr Glu Ala Pro Ala Pro Ala Ser Ser Thr Pro Gln Glu
            195                 200                 205

Pro Trp Pro Gly Pro Thr Ala Pro Ser Pro Thr Ser Arg Pro Pro Trp
        210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Ser Arg Thr Ser Ile Val Gln Ala Ala Ala Gly Val Pro Gly Gly
            260                 265                 270

Gly Ser Asn Asn Gly Lys Thr Pro Val Cys His Gln Cys His Lys Val
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Ile Thr Gly Glu Ile
            340                 345                 350

Met His Ala Leu Lys Met Thr Trp His Val His Cys Phe Thr Cys Ala
        355                 360                 365

Ala Cys Lys Thr Pro Ile Arg Asn Arg Ala Phe Tyr Met Glu Glu Gly
    370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Arg Pro Leu
        435                 440                 445

Cys Lys Ser His Ala Phe Ser His Val
    450                 455

<210> SEQ ID NO 38
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Pro Gln Lys Ala Ser Ala Pro Ala Ala Asp Pro Pro Arg Tyr Thr
1               5                   10                  15

Phe Ala Pro Ser Val Ser Leu Asn Lys Thr Ala Arg Pro Phe Gly Ala
                20                  25                  30

Pro Pro Ala Asp Ser Ala Pro Gln Gln Asn Gly Gln Pro Leu Arg
            35                  40                  45

Pro Leu Val Pro Asp Ala Ser Lys Gln Arg Leu Met
        50                  55                  60
```

```
<210> SEQ ID NO 39
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Pro Ser Val Ser Leu Asn Lys Thr Ala Arg Pro Phe Gly Ala Pro
 1               5                  10                  15

Pro Pro Ala Asp Ser Ala Gly Gly Arg Arg Gln Arg Arg Thr Ser Lys
            20                  25                  30

Leu Met Lys Arg
        35

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Pro Gln Lys Ala Ser Ala Pro Ala Ala Asp Pro Pro Arg Tyr Thr
 1               5                  10                  15

Gly Ala Pro Ser Val Ser Gly Gly Arg Arg Gln Arg Arg Thr Ser Lys
            20                  25                  30

Leu Met Lys Arg
        35

<210> SEQ ID NO 41
<211> LENGTH: 54
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Ser Ala Pro Ala Ala Asp Pro Pro Arg Tyr Thr Phe Ala Pro Ser
 1               5                  10                  15

Val Ser Leu Asn Lys Thr Ala Arg Pro Phe Gly Ala Pro Pro Pro Ala
            20                  25                  30

Asp Ser Ala Pro Gln Gln Asn Gly Gly Gly Arg Arg Gln Arg Arg Thr
        35                  40                  45

Ser Lys Leu Met Lys Arg
    50

<210> SEQ ID NO 42
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ala Pro Pro Pro Ala Asp Ser Ala Pro Gln Gln Asn Gly Gln Pro
 1               5                  10                  15

Leu Arg Pro Leu Val Pro Asp Ala Ser Lys Gln Arg Leu Met Gly Gly
            20                  25                  30
```

```
Arg Arg Gln Arg Arg Thr Ser Lys Leu Met Lys Arg
        35                  40

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gccggccggc cggccggccg gccggccggc cggccg                                    36
```

What is claimed is:

1. A method for inducing deposition and maturation of bone in a subject having a compromised bone condition comprising a co-therapeutic regimen, wherein:
    a) an LMP-1 protein or a fragment thereof that induces bone formation, either optionally with a PTD attached, and
    b) a BMP-2 protein, or an osteogenic fragment thereof, are administered to a targeted site of said subject in amounts effective to induce deposition and maturation of bone.

2. The method of claim 1, wherein said LMP-1 protein or the fragment thereof is administered before said BMP-2 protein or the osteogenic fragment thereof.

3. The method of claim 1, wherein said LMP-1 protein or the fragment thereof is administered after said BMP-2 protein, or the osteogenic fragment thereof.

4. The method of claim 1, wherein the LMP-1 protein or the fragment thereof is administered simultaneously with said BMP-2 protein, or the osteogenic fragment thereof.

5. The method of claim 4, wherein said LMP-1 protein or the fragment thereof and said BMP-2 protein, or the osteogenic fragment thereof is administered as an osteogenic composition.

6. The method of claim 1, wherein the targeted site is selected from the group selected from the group consisting of the intervertebral space, a facet joint, a site of a bone fracture, bones of the mouth, chin and jaw, and an implant site.

7. The method of claim 1, wherein said administration is selected from the group consisting of intrathecal injection, subcutaneous, intravenous, intraperitoneal, intramuscular injection, in an implant and combinations of the above.

8. The method of claim 1, wherein said effective amount of the BMP-2 protein is less than 1.5 mg/mL of bone formed.

9. The method of claim 1, wherein the effective amount of the BMP-2 protein is less than 0.15 mg/mL of bone formed.

10. The method of claim 1, where the PTD is the HIV-TAT protein.

11. The method of claim 1, wherein said BMP-2 protein, or the osteogenic fragment thereof is selected from the group consisting of a functional fragment of a BMP-2 protein, a functional fragment of a BMP-2 protein with a PTD attached, a BMP-2 protein, a functional fragment of an BMP-2 protein variant, a functional fragment of a BMP protein variant with a PTD attached, and a BMP-2 protein variant.

12. The method of claim 1, wherein the condition is selected from the group consisting of broken bones, bone defects, bone transplant, bone grafts, bone cancer, joint replacements, joint repair, fusion, facet repair, bone degeneration, dental implants and repair, bone marrow deficits and other conditions associated with bone and boney tissue.

13. The method of claim 12, wherein the bone defect is a gap, deformation or a nonunion fracture in a bone.

14. The method of claim 12, wherein the bone degeneration is due to osteopenia or osteoporosis.

15. The method of claim 12, wherein the bone defect is due to dwarfism.

16. The method of claim 12, wherein the joint replacement is selected from the group consisting of vertebral, knee, hip, tarsal, phalangeal, elbow, ankle or other articulating joint.

17. The method of claim 12, wherein the joint repair is selected from the group consisting of vertebral, knee, hip, tarsal, phalangeal, elbow, ankle, sacroiliac joint.

18. A method for decreasing the time required to form new bone in the presence of a BMP-2 protein or an osteogenic fragment thereof comprising co-administering to a subject in need thereof an LMP-1 protein or a fragment thereof that induces bone formation, either optionally with a PTD attached.

19. The method of claim 18, wherein the BMP-2 protein, or the osteogenic fragment thereof is selected from the group consisting of an endogenous BMP-2 protein, or an osteogenic fragment thereof, an exogenous BMP-2 protein, or an osteogenic fragment thereof, and an exogenous BMP-2 protein variant, or an osteogenic fragment thereof.

* * * * *